(12) United States Patent
North et al.

(10) Patent No.: US 7,790,162 B2
(45) Date of Patent: Sep. 7, 2010

(54) COMPOSITIONS AND USES THEREOF FOR IDENTIFYING AND TARGETING PROVASOPRESSIN-EXPRESSING CANCER CELLS

(75) Inventors: William G. North, Hanover, NH (US); Brendan P. Keegan, Lebanon, NH (US); Lyn Oligino, South Burlington, VT (US)

(73) Assignee: Woomera Therapeutics, Inc., Lebanon, NH (US)

( * ) Notice: Subject to any disclaimer, the term of this patent is extended or adjusted under 35 U.S.C. 154(b) by 1114 days.

(21) Appl. No.: 10/521,091

(22) PCT Filed: Jul. 16, 2003

(86) PCT No.: PCT/US03/22264

§ 371 (c)(1),
(2), (4) Date: Oct. 11, 2005

(87) PCT Pub. No.: WO2004/006860

PCT Pub. Date: Jan. 22, 2004

(65) Prior Publication Data

US 2008/0050376 A1    Feb. 28, 2008

Related U.S. Application Data

(60) Provisional application No. 60/396,121, filed on Jul. 16, 2002.

(51) Int. Cl.
*A61K 38/00* (2006.01)
*C07H 21/04* (2006.01)
*G01N 33/53* (2006.01)

(52) U.S. Cl. .............. 424/133.1; 424/141.1; 530/387.3; 530/388.9

(58) Field of Classification Search .............. 424/133.1, 424/153.1, 141.1; 530/387.3, 388.9
See application file for complete search history.

(56) References Cited

U.S. PATENT DOCUMENTS 5,530,101 A * 6/1996 Queen et al. ............. 530/387.3

OTHER PUBLICATIONS

North et al. (Breast Can. Res. Treat. 34(3):229-235 (1995)).*
ATCC search for PTA-5322 deposit (Nov. 23, 2008) p. 1.*
ATCC search for MAG-1 antibody (Nov. 23, 2008) p. 1.*
Fundamental Immunology 242 (William E. Paul, M.D. ed., 3d ed. 1993).*
Lipman et al. (ILAR J. 46(3):258-268 (2005)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Dufner (Trends Biotechnol. 24(11):523-29 (2006)).*
Adams, G.P., et al., "High Affinity Restricts the Localization and Tumor Penetration of Single-Chain Fv Antibody Molecules," Cancer Res., 61:4750-4755 (2001).
Camier, M., et al., "Evidence for Higher Molecular Weight Immunoreactive Forms of Vasopressin in the Mouse Hypothalamus," FEBS Lett., 108(2):369-373 (1979).
De Paepe, B., et al., "Growth stimulatory angiotensin II type-1 receptor is upregulated in breast hyperplasia and in situ carcinoma but not in invasive carcinoma," Histochem Cell Biol, 116:247-254 (2001).
Drobnik, J., et al., "Response of Aorta Connective Tissue Matrix to Injury Caused by Vasopressin-Induced Hypertension or Hypercholesterolemia," J. Physiol. Pharmacol., 51(3):521-533 (2000).
Du, J., et al., "Key peptide processing enzymes are expressed by breast cancer cells," Cancer Letters, 165:211-218 (2001).
Fay, M.J., et al., "Evidence for Expression of Vasopressin $V_2$ Receptor mRNA in Human Lung," Peptides, 17(3):477-481 (1996).
Giudice, L.C., and Chaiken, I.M., "Cell-Free Biosynthesis of Different High Molecular Weight Forms of Bovine Neurophysins I and II Coded by Hypothalamic mRNA," J. Biol. Chem., 254(23):11767-11770 (1979).
Johnson, B.E., "Second Lunch Cancers in Patients After Treatment for an Initial Lung Cancer," J. Natl. Cancer Inst., 90(18):1335-1345 (1998).
Junker, K., et al., "Pathology of small-cell lunch cancer," J Cancer Res Clin Oncol, 126:361-368 (2000).
Keegan, B.P., et al., "Targeting the Neurophysin-related Cell Surface Antigen on Small Cell Lung Cancer Cells Using a Monoclonal Antibody against the Glycopeptide Region (MAG-1) of Provasopressin," Molecular Cancer Therapeutics, 1:1153-1159 (2002).
Kortt., A.A., et al., "Dimeric and trimeric antibodies: high avidity scFvs for cancer targeting," Biomol. Eng., 18:95-108 (2001).
Lauber, M., et al., "Immunological and Biochemical Characterization of Distinct High Molecular Weight Forms of Neurophysin and Somatostation in Mouse Hypothalmus Extracts," FEBS Lett., 97(2):343-347 (1979).
Lauber, M., et al., "The Mr 80,000 common forms of neurophysin and vasopressin from bovine neurohypophysis have corticotropin- and β-endorphin-like sequences and liberate by proteolysis biologically active corticotropin," Proc. Natl. Acad. Sci. USA, 78(10):6086-6090 (1981).
Lin, C., et al., "Cell-Free Synthesis of Putative Neurophysin Precursors from Rat and Mouse Hypothalamic Poly(A)-RNA," Biochem. Biophys. Res. Commun., 89(3):943-950 (1979).
Nicolas, P., et al., "Immunological identification of high molecular weight forms common to bovine neurophysin and vasopressin," Proc. Natl. Acad. Sci. USA, 77(5):2587-2591 (1980).

(Continued)

*Primary Examiner*—Lynn Bristol
(74) *Attorney, Agent, or Firm*—Ropes & Gray LLP

(57) ABSTRACT

The present invention discloses antibodies, antigen binding fragments, peptides and peptidomimetics immunoreactive with provasopressin and compositions thereof, methods of phenotyping tissue samples, methods of treating cancer, and kits for phenotyping test biopsy samples and bodily fluids for breast cancer, small cell lung cancer, ductal carcinoma in situ, and atypical ductal hyperplasia.

10 Claims, 8 Drawing Sheets

OTHER PUBLICATIONS

North, W.G., and Yu, X., "Forms of neurohypophysial peptides generated by tumors, and factors regulating their expression," Regulatory Peptides, 45:209-216 (1993).

North, W.G., et al., "Tumor Biosynthesis of Vasopressin and Oxytocin," Ann. NY Acad. Sci., 689:107-121 (1993).

North, W.G., et al., "All three vasopressin receptor sub-types are expressed by small-cell carcinoma," Adv. Exp. Med. Biol., 449:335-338 (1998).

North, W.G., et al., "Functional Vasopressin $V_1$ Type Receptors are Present in Variant as Well as Classical Forms of Small-Cell Carcinoma," Peptides, 18(7):985-993 (1997).

North, W.G., and Du, J., "Key Peptide Processing Enzymes Are Expressed by a Variant Form of Small-Cell Carcinoma of the Lung," Peptides, 19(10):1743-1747 (1998).

North, W.G., et al., "Characterization of an antiserum used in a radioimmunoassay for arginine-vasopressin: implications for reference standards," (Abstract) Endocrinology, 103:1976-1984 (1978).

North, W.G., and Yu, X., "Vasopressin mRNA and Neurophysin-Related Cell-Surface Antigen (NRSA) in Small-Cell Carcinoma," Peptides, 14:303-307 (1993).

North, W.G., "Gene regulation of vasopressin and vasopressin receptors in cancer," Exp. Physiol., 85S:27S-40S (2000).

North, W.G., et al., "Expression of all known vasopressin receptor subtypes by small cell tumors implies a multifaceted role for this neuropeptide," (Abstract) Cancer Research, 58(9):1866-1871 (1998).

North, W.G., et al., "MCF-7 breast cancer cells express normal forms of all vasopressin receptors plus an abnormal $V_2R$," Peptides, 20:837-842 (1999).

North, W.G., et al., "Vasopressin gene related products are markers of human breast cancer," Breast Cancer Research and Treatment, 34:229-235 (1995).

Patel, K.V., et al., "Stimulation or endothelin-1 secretion by human breast cancer cells through protein kinase A activiation: a possible novel paracrine loop involving breast fibroblast-derived prostaglandin $E_2$," Molecular and Cellular Endocrinology, 126:143-151 (1997).

Reynolds, S.D., et al., "Conditional Clara cell ablation reveals a self-renewing progenitor function of pulmonary neuroendocrine cells," Am J Physiol Lung Cell Mol Physiol, 278:L1256-L1263 (2000).

Rosenior, J.C., et al., "Putative precursors of vasopressin, oxytocin, and neurophysins in the rat hypothalamus," (Abstract) Endocrinology, 109:1067-1072 (1981).

Schmale, H., et al., "Cell-free translation of bovine hypothalamic mRNA: synthesis and processing of the prepro-neurophysin I and II," FEBS Letters, 108(2):311-316 (1979).

Taniyama, T., and Watanabe, T., "Monoclonal antibody against human macrophages/monocytes and granulocytes," (Abstract) Hybridoma, 2(2):161-168 (1983).

Todorovska, A., et al., "Design and application of diabodies, triabodies and tetrabodies for cancer targeting," J. Immunol. Methods, 248:47-66 (2001).

Zangemeister-Wittke, U., and Stahel, R.A., "Novel approaches to the treatment of small-cell lung cancer," Cell. Mol. Life Sci., 55:1585-1598 (1999).

Database Pubmed [Online] XP002982655 Retrieved from NCBI Database accession No. 6205974.

Birnbaumer, et al. "The human ADH receptor: the gene, the cDNA, the protein." Vasopressin. P. Gross, D. Richter, G.L. Robertson eds, 1993, John Libbey Eurotext, pp. 19-31.

Friedmann, et al. "Vasopressin and oxytocin production by non-neuroendocrine lung carcinomas: an apparent low incidence of gene expression." Cancer Letters 75 (1993) 79-85.

Friedmann, et al. "Factors Regulating the Production of Vasopressin-Associated Human Neurophysin by Small-Cell Carcinoma of the Lung: Evaluation by Computer-enhanced Quantitative Immunocytochemistry." Neuropeptides (1995) 28, 183-189.

Friedmann, et al. "Products of vasopressin gene expression in small-cell carcinoma of the lung." Br J Cancer (1994) 69, 260-263.

Moore, et al. "Characterization of the "Giant Precursors" (70-80K) of Vasopressin and Oxytocin in the Rat Hypothalamus." The Neurohypophysis: Structure, Function and Control, Progress in the Brain Research, 1983 vol. 60: 253-256.

North, et al. "The Neurophysins: Production and Turnover." The Neurohypophysis: Structure, Function and Control, Progress in Brain Research, 1983, vol. 60: 217-225.

North, William G. "Neuropeptide Production by Small Cell Carcinoma: Vasopressin and Oxytocin as Plasma Markers of Disease." Journal of Clinical Endocrinology and Metabolism, 1991; vol. 73 No. 6: 1316:1320.

North, William G. "Biosynthesis of Vasopressin and Neurophysins." In: D. Gash and G. Boer (eds), Vasopressin: Principles and Properties, pp. 175-209, New York: Plenum Press, 1987.

North, et al; "The Neurophysins and Small Cell Lung Cancer." Greco, FA (ed), Biology and Management of Lung Cancer, 1983, pp: 143-169 Martinus Nijhoff Publishers, Boston.

Terasaki, et al. "Establishment of a Human Small Cell Lung Cancer Cell Line Producing a Large Amount of Anti-diuretic Hormone." Jpn. J. Cancer Res. 85, 718-722, Jul. 1994.

Travis, et al. "Lung Cancer." Cancer Supplement Jan. 1, 1995, vol. 75, No. 1; 191-202.

Waddell, M.D., William J. "A simple ultraviolet spectrophotometric method for the determination of protein." Journal of Laboratory and Clinical Medicine vol. 48, Aug. 1956; 311-314.

Weiner, Louis M. "An Overview of Monoclonal Antibody Therapy of Cancer." Seminars in Oncology vol. 26 Issue 4 suppl 12, Aug. 1999; 41-50.

Wistubab, et al. "Molecular Genetics of Small Cell Lung Carcinoma" Seminars in Oncology vol. 28 Issue 4, Apr. 2001; 3-13.

Taniyama et al., Monoclonal Antibody Against Human Macrophages/Monocytes and Granulocytes. Hybridoma. vol. 2, No. 2 pp. 161-168 (1983).

American Association of Cancer Research 93rd Annual Meeting. p. 971, vol. 42 (2002).

Kotai Kogaku Nyumon (Introduction to Antibody Engineering) pp. 20-22, 104-111, 223-225 (1994).

Miles et al. "Combination versus sequential single-agent therapy in metastatic breast cancer." Oncologist. 2002;7(suppl 6): 13-19.

\* cited by examiner

Figure 2A
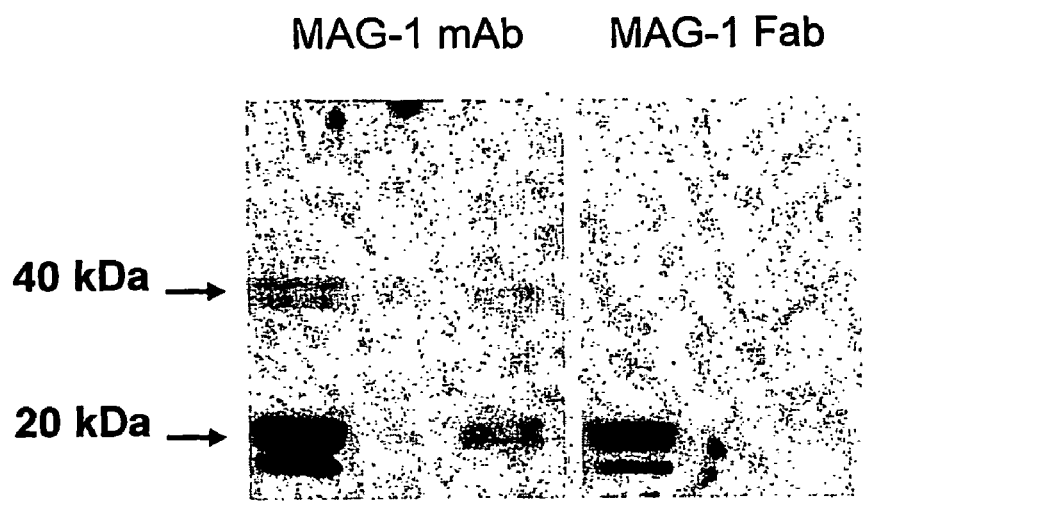
Figure 2B
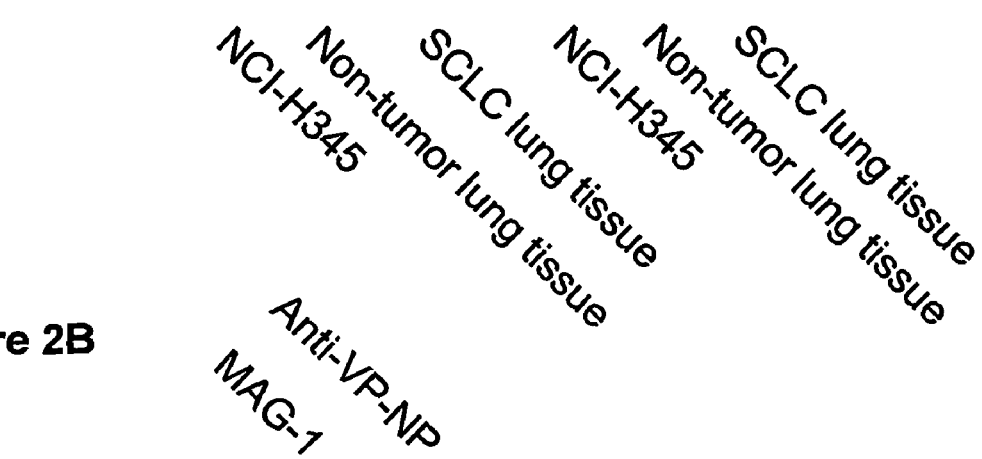
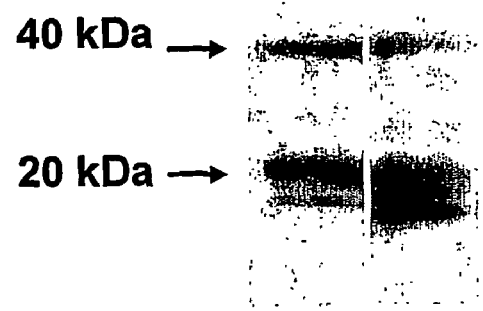
NCI-H82

Figure 3A
NCI-H82
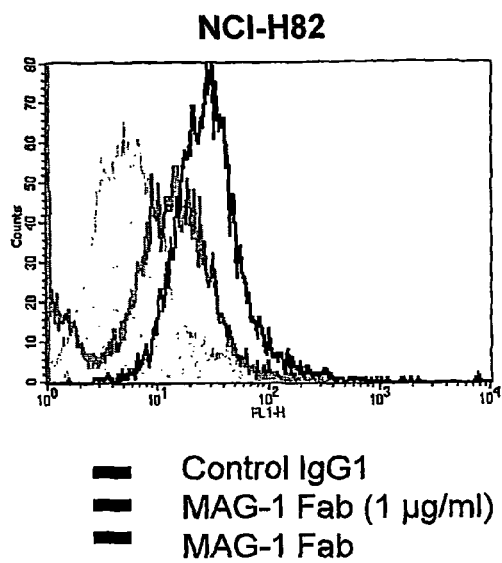
— Control IgG1
— MAG-1 Fab (1 µg/ml)
— MAG-1 Fab
Figure 3B
NCI-
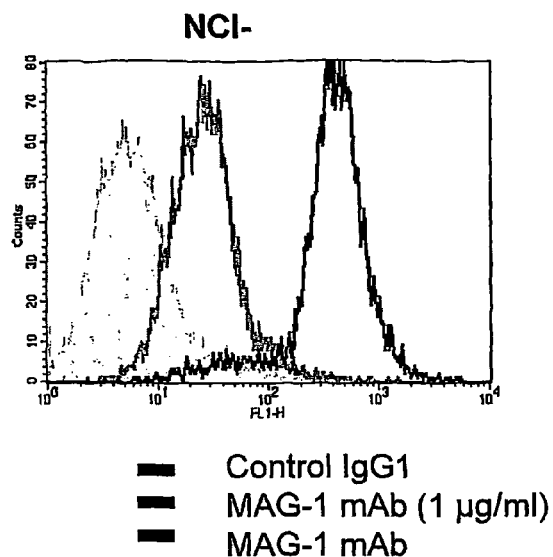
— Control IgG1
— MAG-1 mAb (1 µg/ml)
— MAG-1 mAb
NCI-H345
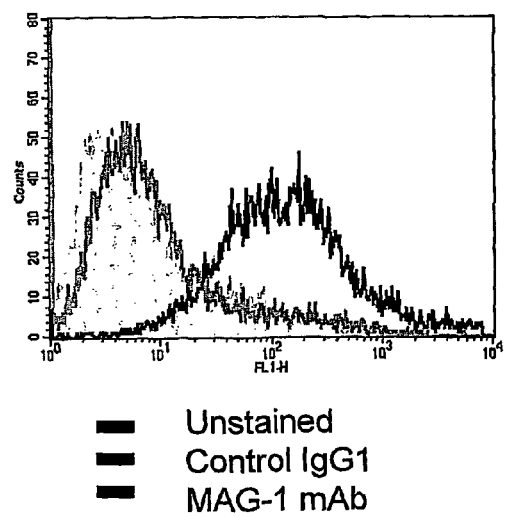
— Unstained
— Control IgG1
— MAG-1 mAb
Figure 3C
Lu-165
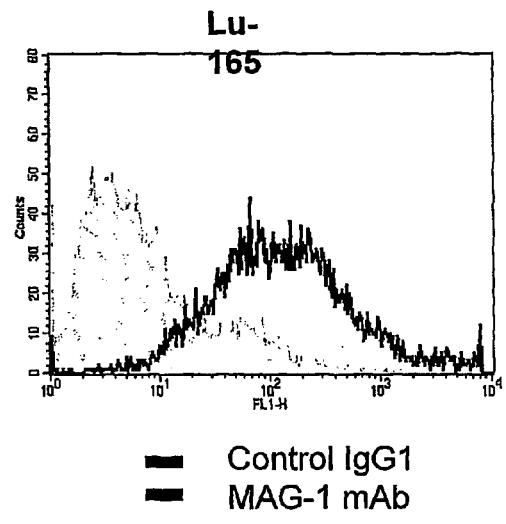
— Control IgG1
— MAG-1 mAb
Figure 3D

Figure 4A
NCI-H82
MAG-1
+
Propidium
Iodide
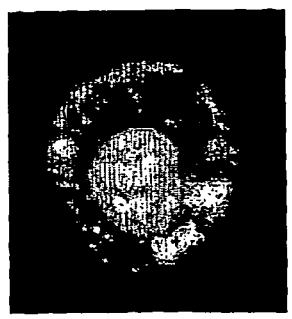
Figure 4B
NCI-H345
Control
IgG1
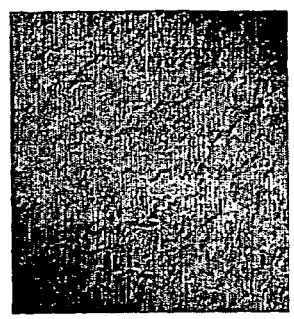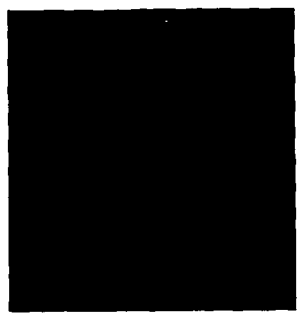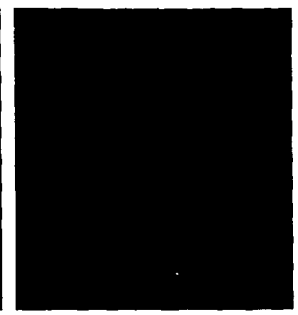
MAG-1
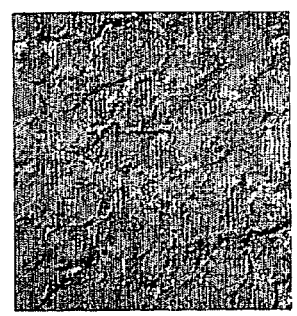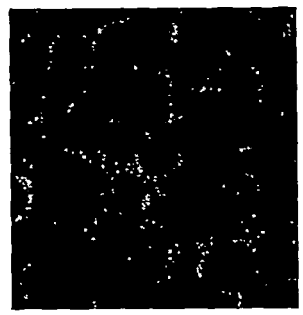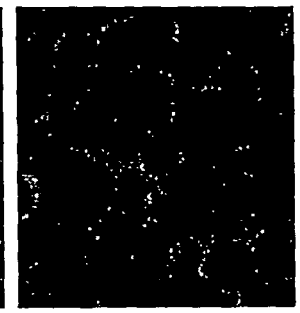
Figure 4C
Lu-165
Control
IgG1
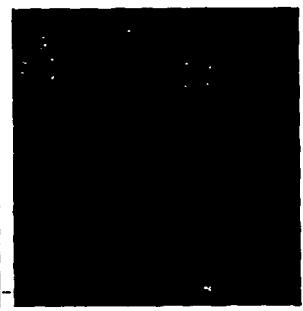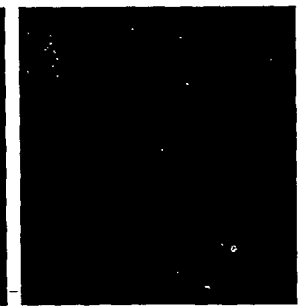
MAG-1
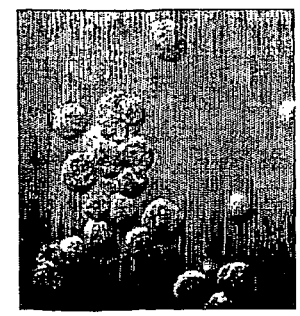

Figure 6A

MKKTAIAIAVALAGFATVAQAEVKLXESGGGLVHPGGSMKLSCVASGFTFS
NYWMNWVRQSPEKGLEWVAEIRLKSNNYATHYAESVKARFTISRDDSKST
VYLQMNNLRGEDTGIYYCTRDVGRDYWGHGSTLTVSGSTSGDIVMTPTPLS
LSVTIGQPASISCKSSQSLLYSNGKTYLNWLQQRPGQAPKHLMYQVSKLDP
GIPDRFSGSGSKTDFTLXISRXEAEDWXVYYCFQGHIIRTRTGXPAGRAX
(SEQ ID NO: 2)

Figure 6B

ATGAAAAAGACAGCTATCGCGATTGCAGTGGCACTGGCTGGTTTCGCTA
CCGTAGCGCAGGCCGAGGTCAAGCTGCNTGAGTCAGGAGGAGGCTTGGT
GCATCCTGGAGGATCCATGAAACTCTCCTGTGTTGCCTCTGGATTCACTT
TCAGTAACTACTGGATGAACTGGGTCCGCCAGTCTCCAGAGAAGGGGCT
TGAGTGGGTTGCTGAAATTAGATTGAAATCTAATAATTATGCAACACATT
ATGCGGAGTCTGTGAAAGCGAGGTTCACCATCTCAAGAGATGATTCCAA
AAGTACTGTCTACCTGCAAATGAACAACTTAAGAGGTGAAGACACTGGC
ATTTATTACTGTACCAGGGACGTGGGACGTGACTACTGGGGCCATGGCT
CCACTCTCACAGTCTCCGGCTCTACTTCCGGTGATATCGTTATGACCCCA
ACTCCACTCTCTTTGTCGGTTACCATTGGACAACCAGCCTCTATCTCTTGC
AAGTCAAGTCAGAGCCTCTTATATAGTAATGGAAAGACATATTTGAATT
GGTTACAACAGAGGCCTGGCCAGGCTCCAAAGCACCTAATGTATCAGGT
GTCCAAACTGGACCCTGGCATCCCTGACAGGTTCAGTGGCAGTGGATCA
AAAACAGATTTTACACCTNAAATCAGCAGAGNGGAGGCTGAAGATTGGG
NAGTTTATTACTGCTTCCAGGGACATATAATCCGTACTCGTACGGGCCCN
CCAGCTGGAAGGGCANNC (SEQ ID NO: 3)

COMPOSITIONS AND USES THEREOF FOR IDENTIFYING AND TARGETING PROVASOPRESSIN-EXPRESSING CANCER CELLS

RELATED APPLICATIONS

This application is a national stage filing under 35 U.S.C. 371 of International Application PCT/US2003/022264, filed Jul. 16, 2003, which claims the benefit of U.S. Provisional Application No. 60/396,121, filed Jul. 16, 2002, each of which is hereby incorporated in its entirety by reference. International Application PCT/US2003/022264 was published under PCT Article 21(2) in English.

FEDERAL FUNDING

Some of the funding for the research leading to the development of the inventions may have been provided under the following Federal research grants: Department of Defense Contract No. DAM D17-94-J-4288; National Cancer Institute Contract Nos. CA 19613 and DK 07508; and Department of Defense Breast Cancer Research Program Fellowship BC011026.

FIELD OF THE INVENTION

The present invention relates to novel compositions and methods for identifying and targeting cancer cells which express vasopressin gene-related surface antigens, and optionally an angiotensin II type-2 receptor. More particularly, the present invention relates to novel monoclonal antibodies and protein fragments which are highly selective for cancer cells which present the proteins structurally related to provasopressin precursor protein as a cell-surface antigen. More particularly, the present invention relates to methods of screening, methods of phenotyping, methods of treatment, and kits.

BACKGROUND OF THE INVENTION

Lung cancer is the leading cause of cancer-related deaths worldwide, and SCLC comprises about 16% of all lung cancer cases in the United States (Travis et al. (1995) *Cancer* 75: 191-202). Currently, SCLC is diagnosed on the basis of gross morphological and histological data, and is too often identified after the disease has reached its advanced stages (Junker et al. (2000) *J. Cancer Res. Clin. Oncol.* 126: 361-368). Although there is a high response rate to present treatments consisting of high-dose chemotherapy with or without radiotherapy, disease recurrence is frequent, and tumors become resistant to these approaches, resulting in 2-year survival rates of only 6-12% (Johnson et al. (1998) *J. Natl. Cancer Inst.* (Bethesda) 90: 1335-1345). Considerable toxicity is also associated with these therapies.

The expression of the vasopressin gene is largely restricted to hypothalamic neurons, and it encodes for a protein product of ~17 kDa, to which an N-glycosidic side-chain of ~4 kDa is added, resulting in the ~20 kDa provasopressin (pro-VP) precursor. This protein is normally packaged into secretory vesicles where it undergoes enzymatic cleavage to generate vasopressin (VP), VP-NP, and VAG (North, W. G. In: D. Gash and G. Boer (eds.), *Vasopressin: Principles and Properties*, pp. 175-209. New York: Plenum Press, 1987). These components are then secreted into the circulation. SCLC tumors and cultured cells also express the VP gene, however intact provasopressin protein can become localized to the cell surface plasma membrane (Friedmann et al. (1994) *B. J. Cancer* 69: 260-263; North et al. (1993) *Ann. NY Acad. Sci.* 689: 107-121). Polyclonal antibodies raised against VP-NP bind specifically to the surface of cultured SCLC cells, as determined by immunofluorescent analysis (Friedmann et al. (1995) *Neuropeptides* 28: 183-189; North et al. (1983) *Prog. Brain Res.* 60: 217-225; North and Yu (1993) *Regulatory Peptides* 45: 209-216). Thus, the target of these antibodies has been termed neurophysin-related cell surface antigen (NRSA) (North et al. (1993) *Peptides* 14: 303-307). Polyclonal anti-VP-NP antibodies recognize proteins of ~20 kDa and ~40 kDa in total protein extracts from SCLC cultured cells by Western analysis (North et al. (1993) *Peptides* 14: 303-307). The ~20 kDa protein corresponds in size to the provasopressin protein, and the ~40 kDa protein is believed to be a related form (Camier et al. (1979) *FEBS Lett.*, 108: 369-373; Lauber et al. (1979) *FEBS Lett.*, 97: 343-347; Lauber et al. (1981) *Proc. Natl. Acad. Sci. USA*, 78: 6086-6090; Moore and Rosenior. (1983) *Prog. Brain Res.*, 60: 253-256; Nicolas et al. (1980) *Proc. Natl. Acad. Sci. USA*, 77: 2587-2591; Rosenior et al. (1981) *Endocrinology*, 109: 1067-1072). Polyclonal antibodies that have been raised against the vasopressin, VP-NP, or VAG regions of the pro-VP protein display specific staining of SCLC tumor sections, whereas they exhibit a very low incidence of immunoreactivity with the non-neuroendocrine tumors examined (Friedmann et al. (1994) *B. J. Cancer* 69: 260-263; Friedmann et al. (1993) *Cancer Letters* 75: 79-85).

Breast cancer is a leading cause of death among women throughout the world, and accounts for the death of approximately 50,000 women in the United States each year (American Cancer Society. Cancer Facts and Figures, Atlanta, Ga.: American Cancer Society, 1993). Although there have been many recent advances for effectively treating this disease (Silverstein, M. J. et al., *The Breast Journal* (2002) 8:70-76), successful intervention still heavily relies on early detection through mammography and surgical removal of cancerous tissue. As for small cell lung cancer (SCLC), products of the vasopressin (VP) gene appear to present a universal tumor marker system for breast cancer/ductal carcinoma in situ (DCIS) that could provide advanced warnings of early post-oncogenic tissue changes, precise methods for identifying and evaluating changes in tumor burden, and new non-surgical methods of treatment that are effective in providing long-term survival for patients (North et al. *Br. Can. Res. Treat.* (1995) 34: 229-235; and North *Exper. Physiol.* (2000) 85S: 27-40). Alternatively, no evidence has been found for expression by normal breast tissues or by various fibrocystic conditions, including atypical hyperdisplasia (North et al., *Endocrin. Pathology*, In Press, June, 2003). Expression of the VP gene in breast cancer gives rise to surface markers named GRSA (North *Exper. Physiol.* (2000) 85S: 27-40). These markers interact with polyclonal antibodies recognizing provasopressin and seem to have molecular weights of 40 and 20 kilodaltons. Since the antibodies were first found to interact with glycopeptide moiety of provasopressin, the antigen has been called GRSA (i.e., Glycopeptide-Related cell Surface Antigen).

SUMMARY OF THE INVENTION

The present invention provides effective therapeutic methods, compositions, diagnostic methods, kits, and pharmaceutical packages for diseases associated with tumor cells.

The compositions according to the invention comprise peptides, antibodies, antigen binding fragments, and peptidomimetics that are immunoreactive with different regions or provasopressin (e.g., vasopressin (VP), neurophysin (NP)

and vasopressin-associated glycopeptide (VAG)), in the cell or as it presents itself as Neurophysin-Related/Glycopeptide-Related Surface Antigen (NRSA/GRSA). Antibodies of the present invention can be monoclonal antibodies which are immunoreactive with a C-terminal epitope of the VAG domain of provasopressin. One embodiment of the present invention is the monoclonal antibody MAG-1. Also encompassed by the present invention are antibodies including an antigen binding site comprising a heavy chain variable region sequence represented in SEQ ID NO: 26 and/or a light chain variable region sequence represented in SEQ ID NO: 27, wherein the antibody is immunoreactive with a C-terminal epitope of the VAG domain of provasopressin. Single chain variable fragment (scFv), a Fab fragment, a F(ab')$_2$ fragment, a heavy chain, and a light chain of the antibodies are encompassed by the present invention, as are humanized antibodies. Antibodies, antigen binding fragments, and peptides of the present invention are immunoreactive with the C-terminal epitope of the VAG domain of provasopressin expressed in invasive breast cancer, ductal carcinoma in situ, and small cell lung cancer.

One embodiment of the present invention includes a method of identifying a patient susceptible to breast cancer or ductal carcinoma in situ comprising obtaining a test sample from a patient, rendering the test sample amenable to immunoassay, contacting the rendered sample with a peptide or an antibody, or an antigen binding fragment under conditions that allow for binding to provasopressin; and determining if the cells of the rendered sample overexpress provasopressin compared to a control tissue, wherein if the test sample overexpresses provasopressin, a patient susceptible to breast cancer or ductal carcinoma in situ has been identified. The test sample can be further reacted with an antibody immunoreactive with the angiotensin II type-2 receptor. If the test sample is positive for staining for provasopressin and negative for staining the angiotensin II type-2 receptor, the test sample is diagnosed as invasive breast cancer. If the test sample is positive for staining both provasopressin and the angiotensin II type-2 receptor, the test sample is diagnosed as ductal carcinoma in situ. If the test sample is negative for staining for provasopressin and positive for staining the angiotensin II type-2 receptor, the test sample is diagnosed as atypical ductal hyperplasia.

One embodiment of the present invention is a kit useful for phenotyping a biopsy tissue sample for breast cancer, ductal carcinoma in situ, and atypical ductal hyperplasia comprising a preparation of an antibody or peptide immunoreactive with provasopressin and a preparation of an antibody immunoreactive with an angiotensin II type-2 receptor. The antibody/peptide preparations can be used in any immunoassay.

If the test biopsy sample is positive for staining for provasopressin and negative for staining the angiotensin II type-2 receptor, the test biopsy sample is phenotyped as an invasive form of breast cancer.

If the test biopsy sample is positive for staining both provasopressin and the angiotensin II type-2 receptor, the test biopsy sample is phenotyped as ductal carcinoma in situ.

If the test biopsy sample is negative for staining for provasopressin and is positive for staining the angiotensin II type-2 receptor, the test biopsy sample is phenotyped as atypical ductal hyperplasia.

The antibody preparation immunoreactive with provasopressin can be polyclonal antibodies, monoclonal antibodies, humanized antibodies, chimeric antibodies, recombinant antibodies, or antigen binding fragments thereof. Antibody preparations of the kit can be monoclonal antibodies, such as a mAb which binds to the C-terminal VAG domain of provasopressin produced by the hybridoma having ATCC No PTA-5322. More specifically, the monoclonal antibody can be MAG-1.

The antibody preparation immunoreactive with the angiotensin II type-2 receptor can be polyclonal antibodies, monoclonal antibodies, humanized antibodies, chimeric antibodies, recombinant antibodies, or antigen binding fragments thereof. More specifically, the antibody preparation immunoreactive with the angiotensin II type-2 receptor is a polyclonal AT$_2$ antibody (Santa Cruz Biotechnology, Santa Cruz, Calif.).

Peptides of the kits of the present invention comprise a portion of provasopressin and are immunoreactive with provasopressin. Preferably, the peptide of the present invention is any one of: TSLSMQYGPLDS (SEQ ID NO: 4); FPFPVRPSPLAM (SEQ ID NO: 5); ILPNTRPSNYLM (SEQ ID NO: 6); HHHRPTPLLQVT (SEQ ID NO: 7); KLKLHDGTPYNL (SEQ ID NO: 8); WQQKGHTPTPMP (SEQ ID NO: 9); QGWPQSSKLGLT (SEQ ID NO: 10); NNQSPHLRPTGS (SEQ ID NO: 11); TTTDMSPHWGLR (SEQ ID NO: 12); TYQSNLGLSSPR (SEQ ID NO: 13); YPYWSNAMSMAS (SEQ ID NO: 14); FPNHALSKRWGI (SEQ ID NO: 15); HQNHLHVPVSWS (SEQ ID NO: 16); TMDPFRSVWPRL (SEQ ID NO: 17); MNYTSTPGPRSW (SEQ ID NO: 18); LLDPYHPRKLSR (SEQ ID NO: 19); IIRGAQVDHSTW (SEQ ID NO: 20); and LWAHSYNFRLLS (SEQ ID NO: 21).

One embodiment of the present invention includes a method of phenotyping breast tissue samples from patients to distinguish fibrocystic and cancerous lesions comprising obtaining a test biopsy sample from a patient, rendering the test biopsy sample amenable to immunoassay, contacting the rendered sample with an antibody or peptide immunoreactive with provasopressin under conditions that allow for binding to provasopressin, contacting the rendered sample with an antibody immunoreactive with an angiotensin II type-2 receptor, and determining if the cells express one of both of provasopressin and angiotensin II type-2 receptor.

If the test biopsy sample is positive for staining for provasopressin and negative for staining the angiotensin II type-2 receptor, the test biopsy sample is phenotyped as an invasive form of breast cancer.

If the test biopsy sample is positive for staining both provasopressin and the angiotensin II type-2 receptor, the test biopsy sample is phenotyped as ductal carcinoma in situ.

If the test biopsy sample does not stain for provasopressin or the angiotensin II type-2 receptor, the test biopsy sample is phenotyped as fibrocystic (e.g., ADH).

Antibody preparations of the present invention can be polyclonal antibodies, monoclonal antibodies, humanized antibodies, chimeric antibodies, recombinant antibodies, or antigen binding fragments thereof. Preferably, antibodies of the methods can be monoclonal antibodies, such as one which binds to the C-terminal VAG domain of provasopressin and is produced by the hybridoma having ATCC No. PTA-5322. More preferably, the monoclonal antibody can be MAG-1. Preferably, the antibody immunoreactive with the angiotensin II type-2 receptor is a polyclonal AT$_2$ antibody (Santa Cruz Biotechnology).

Peptides of the present invention comprise a portion of provasopressin and are immunoreactive with provasopressin. Preferably, the peptide of the present invention is any one of: TSLSMQYGPLDS (SEQ ID NO: 4); FPFPVRPSPLAM (SEQ ID NO: 5); ILPNTRPSNYLM (SEQ ID NO: 6); HHHRPTPLLQVT (SEQ ID NO: 7); KLKLHDGTPYNL (SEQ ID NO: 8); WQQKGHTPTPMP (SEQ ID NO: 9); QGWPQSSKLGLT (SEQ ID NO: 10); NNQSPHLRPTGS (SEQ ID NO: 11); TTTDMSPHWGLR (SEQ ID NO: 12); TYQSNLGLSSPR (SEQ ID NO: 13); YPYWSNAMSMAS (SEQ ID NO: 14); FPNHALSKRWGI (SEQ ID NO: 15); HQNHLHVPVSWS (SEQ ID NO: 16); TMDPFRSVWPRL (SEQ ID NO: 17); MNYTSTPGPRSW (SEQ ID NO: 18); LLDPYHPRKLSR (SEQ ID NO: 19); IIRGAQVDHSTW (SEQ ID NO: 20); and LWAHSYNFRLLS (SEQ ID NO: 21).

BRIEF DESCRIPTION OF THE DRAWINGS

FIG. 2 shows detection of NRSA in cultured SCLC cells and human SCLC tissue by Western analysis. FIG. 2A illustrates staining with MAG-1 mAb or MAG-1 Fab. FIG. 2B illustrates staining with MAG-1 mAb or a rabbit polyclonal antibody against VP-NP. Approximate molecular mass is indicated on the left of each figure. Total cellular or tissue protein extracts (40 μg) were separated by SDS-PAGE, blotted onto polyvinylidene difluoride (PDVF) membrane, and reacted with (A) MAG-1 mAb or MAG-1 Fab, and with (B) MAG-1 mAb or a rabbit polyclonal antibody against VP-NP.

FIG. 3 shows flow cytometry analysis of MAG-1 binding to the surface of cultured SCLC cells. FIG. 3A illustrates MAG-1 Fab staining of NCI-H82 cells at two different concentrations compared to a control IgG1 antibody. FIG. 3B illustrates MAG-1 mAb staining of NCI-H345 cells compared to a control IgG1 antibody. FIG. 3C illustrates MAG-1 mAb staining of NCI-H82 cells at two different concentrations compared to a control IgG1 antibody. FIG. 3D illustrates MAG-1 mAb staining of Lu165 cells compared to a control IgG1 antibody. Antibody staining procedures prior to flow cytometry were performed using conditions that minimize plasma membrane internalization. MAG-1 mAb and MAG-1 Fab were employed at a concentration of 100 μg/ml except where noted.

FIG. 4 shows confocal analysis of MAG-1 binding to the surface of cultured SCLC cells. SCLC cells were reacted with MAG-1 or an isotype control mAb, followed by FITC-labeled secondary antibodies. FIG. 4A illustrates combined differential interference contrast (DIC) transmitted, red fluorescent, and green fluorescent light channel images of NCI-H82 cells viewed with a 40× objective (NA 1.4) and a 5.8× magnification zoom setting. The cells were incubated with propidium iodide to stain the nuclei (gray) for contrast. FIG. 4B NCI-H345 illustrates imaged by confocal microscopy and the top panels display the control IgG1 observed with a 20× objective (0.5 NA) and the lower panels display the MAG-1 stained cells observed with a 40× objective (1.3 NA). FIG. 4C illustrates Lu-165 cells imaged by confocal microscopy with a 40× objective. For FIGS. 4B and 4C, the left panels depict the transmitted light channel images, the middle panes depict the green fluorescent light channel images, and the right panels depict the two combined images.

FIG. 5 illustrates immunohistochemical analysis of human tissue sections using MAG-1 mAb.

FIG. 6 illustrates the amino acid sequence and nucleic acid sequence of a single chain variable fragment immunoreactive with the C-terminal 18-amino acid residues of VAG. FIG. 6A depicts the amino acid sequence (SEQ ID NO: 2). FIG. 6B depicts the nucleic acid sequence (SEQ ID NO: 3).

DETAILED DISCLOSURE OF THE INVENTION

I. Overview

Figure 1:
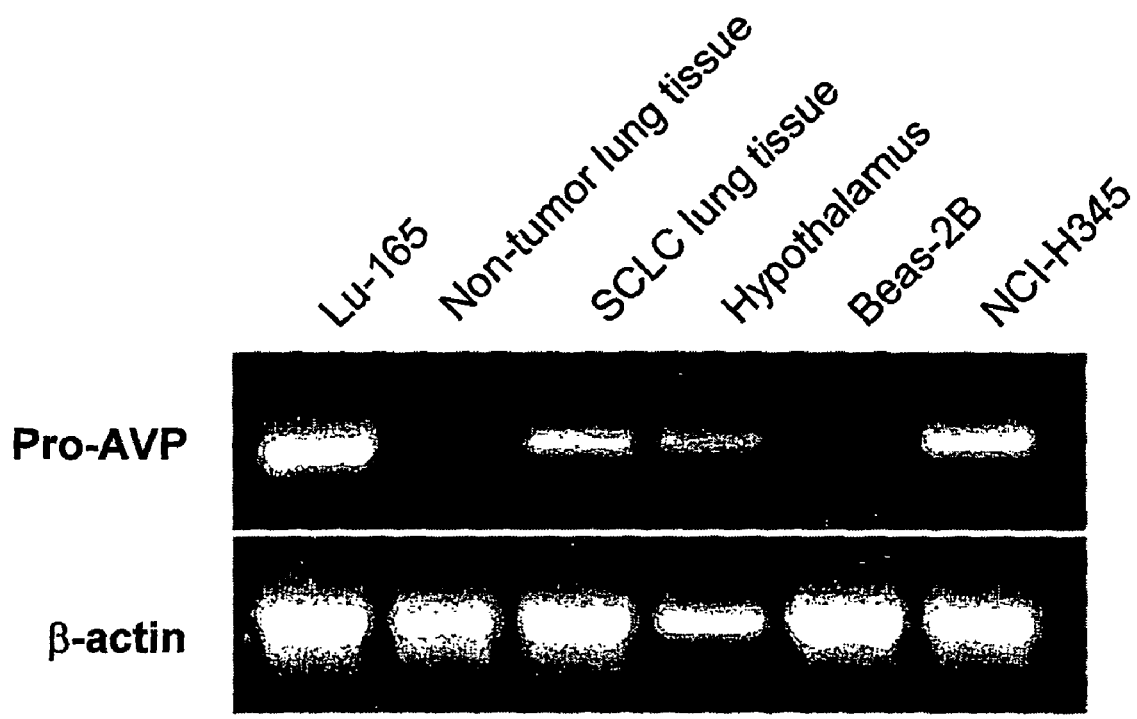
FIG. 1 illustrates detection of NRSA in cultured SCLC cells and human SCLC tissue by RT-PCR analysis. RT-PCR was performed on total RNA extracts from the indicated cell lines or human tissue. Products were separated on a 1.5% agarose gel and visualized with ethidium bromide. The PCR primers were designed to amplify the entire coding region for the pro-VP protein, which spans 2 introns. The predicted size for the amplification is 570 bp. Lu-165 and NCI-H345; SCLC cell lines, Beas-2B; transformed normal human epithelial cell line, lung and hypothalamus; human tissue extracts were tested.

The pressing need for effective screening and non-toxic treatment methods has spawned a search for new approaches to combat breast cancer and small cell lung cancer (SCLC), taking advantage of the numerous molecular and genetic abnormalities that have been described for breast cancer and SCLC (Junker et al. (2000) *J. Cancer Res. Clin. Oncol.* 126: 361-368; Wistuba et al. (2001) *Semin. Oncol.* 28: 3-13 2001; Zangemeister-Wittke and Stahel (1999) *Cell. Mol. Life Sci.* 55: 1585-1598; and Popescu N C and Zimonjic D B (Oct. 30, 2002) *Am. J. Med. Genet.* 115(3): 142-149). The prospect of antibodies directed against cell-surface tumor-specific antigens is attractive not only for use in the differential diagnosis of SCLC, but also for use in localizing and eradicating tumors since they have the potential for eliciting minimal side effects (Weiner, L. M. (1999) *Semin. Oncol.* 26: 41-50). This strategy is most effective when directed against tumor-specific antigens that are not lost or modulated, and products of the vasopressin gene may provide for such an antigen.

The present invention discloses the detection of NRSA in cultured SCLC cells and human SCLC tumor tissue using a mAb designated MAG-1, which was generated using a synthetic peptide representing the C-terminal portion of the VAG region of the pro-VP protein. MAG-1 recognizes the ~20 kDa and ~40 kDa NRSA proteins in cultured SCLC cell lysate by Western analysis, while immunofluorescent cytometric and microscopic analyses indicates that it binds to the surface of these cells. More importantly, the ~20 kDa and ~40 kDa NRSA proteins were detected in the lysate of human SCLC tumor biopsy samples by Western analysis using MAG-1, but they were not detected in the lysate of non-tumor human lung tissue. Immunohistochemical analysis revealed that MAG-1 reacts with human SCLC tumor, but not with normal lung tissue. Since NRSA is not typically found on the surface of normal cells, it is anticipated that it can serve as an excellent target in a MAG-1-based approach for tumor localization in the diagnosis and therapy of SCLC.

Currently, screening for breast cancer requires direct immunohistochemistry and a battery of antibodies directed against several tumor markers which individually occur in less than 50% incidence in these tumors.

It is currently very difficult for pathologists to distinguish invasive breast cancer and ductal carcinoma in situ from atypical ductal hyperplasia, and a method for achieving this is urgently needed because it can save women undergoing unnecessary surgery. A diagnosis of the former will generally result in surgery, a diagnosis of the latter, in no intervention.

One embodiment of the present invention encompasses a monoclonal antibody (MAG-1) directed to the C-terminal region of the glycopeptide component of the provasopressin protein (VAG), and that the two major immunoreactive forms of NRSA are detected using MAG-1 in protein extracts from cultured SCLC cells as well as in protein extract from human SCLC tumor. However, these proteins were not detected in protein extract from non-tumor human lung tissue by Western analysis using MAG-1. Some cancers, including SCLC, are known to express the vasopressin gene, although it appears that not all of the precursor protein is enzymatically processed and secreted into the circulation as in the hypothalamus. Polyclonal anti-VP-NP antibodies have been shown to recognize proteins ~20 kDa and ~40 kDa in SCLC cell extracts (North et al., (1993) Peptides 14: 303-307). The predicted size of the glycosylated pro-VP protein product of the normal VP message is ~20 kDa, and this has been demonstrated using a cell-free translation assay (Giudice et al. (1979) J. Biol. Chem. 254: 11767-11770; Lin et al. (1979) Biochem. Biophys. Res. Commun. 89: 943-950; Schmale et al. (1979) FEBS Lett. 108: 311-316). Previous studies identified an extended VP message which was though might account for the ~40 kDa protein (North et al., (1993) Peptides 14: 303-307; Rosenbaum et al. (1990) PNAS 87: 9928-9932). However, only one form of the predicted size for the normal VP message was detected by RT-PCR in the SCLC cell lines and tumor tissue used in this study, and this corresponded in size to that detected in human hypothalamus.

Polyclonal antibody preparations were shown to specifically stain human SCLC and hypothalamus tissue sections, as well as bind to the plasma membrane of cultured SCLC cells in a similar manner to what was observed using MAG-1 (Friedmann et al. (1994) Br. J. Cancer 69:260-263; Friedmann et al. (1995) Neuropeptides 28: 183-189; North and Yu (1993) Regulatory Peptides 45: 209-216; Friedmann et al. (1993) Cancer Lett. 75: 79-85; North et al. (1983) In: F. Greco (ed.), Biology and Management of Lung Cancer, pp. 143-169. Boston: Martinus Nijhoff). We have determined that the ~20 kDa and ~40 kDa NRSA proteins are VP gene related products can serve as tumor-specific antigens and can be targeted by antibodies (North and Yu (1993) Regulatory Peptides 45: 209-216; North et al. (1993) Peptides 14: 303-307; North, W. G., et al. (1995) Breast cancer Research and Treatment 34:229-235; Friedmann et al. (1994) Br. J. Cancer 69:260-263; Friedmann et al. (1993) Cancer Lett. 75: 79-85; North et al. (1989) Nuc. Med. Commun. 10: 643-652).

Although the level of NRSA expression by the different SCLC cell types has not been measured, we demonstrated that MAG-1 can recognize NRSA on the surface of cultured cell lines derived from SCLC tumors of both the classical and variant sub-types. Fluorescent microscopy revealed that MAG-1 staining was observed with each SCLC cell type examined with differing levels of immunoreactivity.

Additionally, we demonstrated the specificity of MAG-1 for SCLC tumor by immunohistochemical analysis. MAG-1 reacted with human SCLC tumor, but not with normal lung tissue. The staining appeared to be localized to the surface, as well as the cytoplasm on the SCLC cells in the section of tumor. MAG-1 also reacted with human hypothalamus tissue, the staining appeared to be localized to the cytoplasm. These results indicate that MAG-1 can be used to effectively target NRSA on SCLC tumors. MAG-1 did not react with the normal lung epithelial cells in the tissue used in the immunohistochemical screening, however staining was observed in pulmonary neuroepithelial bodies. Although not obvious in the figure, VP message was detected in the non-tumor lung sample used in the RT-PCR reaction (FIG. 1).

Figure 5A:
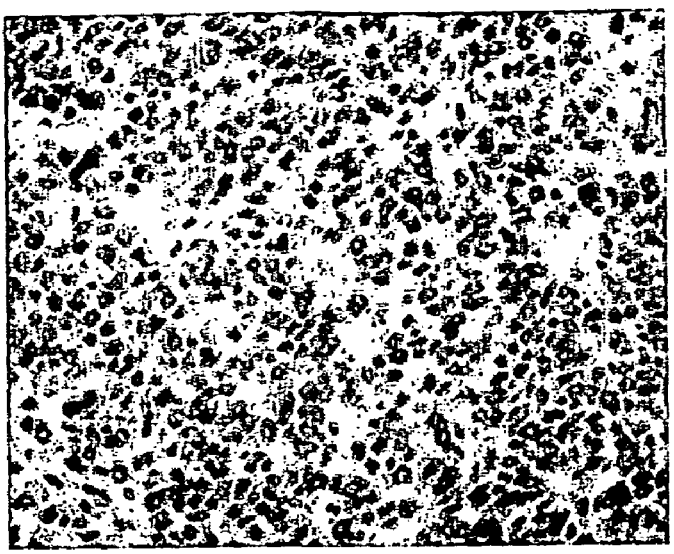
FIG. 5A depicts MAG-1 immunoreactivity with human SCLC tumor cells (brown staining).
Figure 5B:
FIG. 5B depicts control normal epithelial cells of the alveoli of the lung.

The expression of the VP message could represent the presence of pulmonary neuroendocrine cells in the lung tissue sample used (Reynolds et al. (2000) Am. J. Physiol. Lung Cell. Mol. Physiol. 278: L1256-L1263), but the prohormone may be enzymatically processed and the products secreted as occurs in the hypothalamus. This theory is supported by the immunohistochemical findings depicted in FIG. 5.

The potential uses for the MAG-1 mAb are significant, not only as a tumor-targeting agent for the localization and treatment of SCLC, but also for distinguishing SCLC from other forms of lung cancer, and aiding its early diagnosis (Friedmann et al. (1994) Br. J. Cancer 69:260-263; Friedmann et al. (1993) Cancer Lett. 75: 79-85; North et al. (1989) Nuc. Med. Commun. 10: 643-652). The ability of the MAG-1 Fab fragment to recognize synthetic antigen, as well as NRSA in protein extracts from SCLC tumor and cultured cells was also evaluated since antibody fragments may be better suited for some in vivo applications. While the Fab was able to recognize NRSA by Western analysis, not surprisingly it displayed a lower binding affinity for synthetic antigen. However, the localization of antibody molecules to tumor tissue, and their ability to penetrate solid tumor depends on a number of factors including size, affinity, rate of clearance, and antigen density (Adams et al. (2001) Cancer Res. 61: 4750-4755; Todorovska et al. (2001) J. Immunol. Methods 248: 47-66).

Variable region fragments (Fv) of this antibody have been produced to assess their potential for in vivo tumor targeting because they may provide additional benefits for use in imaging and therapy (Kortt et al. (2001) Biomol. Eng. 18: 95-201).

NRSA is not typically found on the surface of normal cells, it is not modulated between classical and variant SCLC, and there is a low incident of its expression by non-neuroendocrine lung carcinomas (Friedmann et al. (1993) Cancer Letters 75: 79-85). Therefore, NRSA should serve as an excellent target for the localization of SCLC tumors in diagnosis and therapy, employing MAG-1 mAb and its fragments.

This invention pertains to the discovery of the provasopressin precursor protein as a novel tumor specific marker that can be targeted with antibodies, antibody fragments, their derivatives (such as monospecific or bispecific scFv fragments or Fd fragments), or binding peptides. To date we have screened 70 small cell lung cancer (SCLC), 62 breast cancer, and 55 ductal carcinoma in situ (DCIS) human tissue sections with various antibodies to provasopressin, and they all have displayed positive staining. Normal lung and breast tissue sections, including ADH sections, do not display staining with these antibodies. The discovery that the provasopressin precursor protein can be used as a specific tumor antigen constitutes a novel finding. The concept to develop of antibodies, antibody fragments, their derivatives, or binding peptides for use in targeting cancers that express the provasopressin precursor protein, for the purpose of research, early detection, diagnosis, therapy, and prevention represent direct applications of that finding.

Under normal physiological conditions, the vasopressin gene is expressed for the most part by hypothalamic neurons, where the resultant provasopressin precursor protein is enzymatically cleaved into its peptide hormone components, which include the neuropeptide vasopressin (VP), vasopressin-associated neurophysin (VP-NP), and vasopressin-associated glycopeptide (VAG). Certain cancers, including small-cell lung cancer (SCLC), and breast cancer, also express the vasopressin gene, and vasopressin production by tumors has been described in the literature beginning around the early 1970s, where elevated levels of vasopressin were detected in the blood of patients with SCLC. However, North et al. first described the possibility that the provasopressin precursor protein could localize to the surface of cancer cells, and serve as a tumor antigen, in 1983. The terms Neurophysin- and Glycopeptide-Related Cell-Surface antigen (NRSA and GRSA) were applied to the provasopressin precursor protein as it presents itself as a useful antigen for tumor targeting. The difference in the terminology stemmed from the use of antibodies directed against two different regions of the provasopressin protein.

Antibodies can be used for targeting provasopressin (NRSA/GRSA) on tumors. Previous work indicates that SCLC tumors can be localized and imaged in humans using radiolabeled antibody directed against the neurophysin portion of provasopressin. Subsequent studies show that polyclonal antibodies, monoclonal antibodies, and antibody Fab fragments directed against different regions of the provasopressin protein bind specifically to cultured SCLC and breast cancer cells, as well as to human tumor sections, but not to tissue that is devoid of tumor. We have developed polyclonal and monoclonal antibodies, and their Fab fragment derivatives, to NRSA/GRSA and have demonstrated that they can bind to cultured human cancer cells and human cancer tissue. Since the NRSA/GRSA is not typically found in normal cells, it is anticipated that it can serve as an excellent target for tumor localization in the early detection, diagnosis, and treatment of cancers that express the vasopressin gene. NRSA/GRSA also provides for a attractive candidate for use in vaccine development strategies for the prevention of those cancers that express the vasopressin gene.

Single-chain antibodies fragments and small binding peptides can be used for targeting provasopressin (NRSA/GRSA) on tumors. We have produced single-chain variable region fragments (scFv) of an antibody, as well as peptides, that bind to NRSA/GRSA. The use of such smaller molecules will provide added benefits (tumor penetration, ease of manufacturing) for in vivo tumor targeting. Although the expression of vasopressin by various tumors has been known for some time, targeting the precursor protein with antibodies and antibody fragments is a novel concept.

Mechanisms of vasopressin gene expression can be targeted for tumor therapy. Additionally, vasopressin is involved in autocrine regulation of tumor survival, and preliminary results demonstrate that the vasopressin MRNA message is a viable target for antisense-based methods for the inhibition of tumor growth.

The term "Immuno-based" refers to the use of antibodies, antibody fragments, their derivatives, or binding peptides.

1.) Early Detection a.) Measurement blood levels of provasopressin components for indication of certain tumors. Antibodies directed against various portions of the provasopressin precursor protein would be useful in the clinical screening assay to measure their levels in the blood of patients suspected of having certain tumors, or who have had those tumors in the past. This would be a useful, non-invasive or less invasive test to possibly justify further, more invasive tests/biopsies, and aid in monitoring recurrence of disease.

b.) Immuno-based imaging. With the use of antibodies directed against various portions NRSA/GRSA, current imaging techniques, such as mammography, could be greatly enhanced, and new imaging protocols for diseases such as SCLC/breast cancer could be developed and effectively implemented for clinical use. These types of techniques would be especially useful for the detection of metastatic disease.

2.) Diagnosis a) Immuno-based pathological screening of biopsies. Currently, SCLC is diagnosed on the basis of gross morphological and histological data obtained from biopsied tissue, and is far too often identified after the disease has reached its advanced stages. Additionally, DCIS is often difficult to discern from atypical ductal hyperplasia (ADH), generally considered to be a benign affliction, on biopsied tissue sections. These biopsied tissue samples can be stained using antibodies directed against various portions NRSA/GRSA, allowing for critical differential diagnoses to be made, which can then effect subsequent treatment procedures and outcomes.

b.) In situ immuno-based imaging. Similar to that outlined in 1.a. above, the use of antibodies directed against various portions NRSA/GRSA could be used in combination with mammographic imaging techniques to allow for non-invasive or less invasive diagnoses of breast disease versus hyperplastic conditions.

Compositions of the present invention can be used for immuno-based targeting of tumors and delivery of chemotoxic/radiologic agents. As mentioned above, SCLC tumors can be localized and imaged using an antibody to the neurophysin region of the provasopressin protein. Thus, antibodies, antibody fragments, their derivatives, or binding peptides could be radiolabeled, conjugated to or used in conjunction with chemotoxic agents, or serve as an attractor for endogenous immune system cells to kill NRSA/GRSA-expressing tumors. Since all SCLC, breast cancer, and DCIS cells appear to express NRSA/GRSA, treatments that target this antigen would provide for significantly more potent therapy than currently available strategies for these diseases.

Targeting the inhibition of vasopressin gene transcription and/or vasopressin mRNA message translation to prevent tumor growth. Since vasopressin provides for autocrine growth stimulation in cancer cells that express the vasopressin gene, inhibition of it production would inhibit tumor survival. By using antisense molecules to block gene transcription translation, a powerful, non-invasive tool for therapy could be developed.

Cancer vaccines are based on tumor antigens, such as NRSA and GRSA. Because of its unique expression in certain cancers, vaccine strategies based on NRSA/GRSA, such as anti antibodies or utilizing antigenic motifs on the NRSA/GRSA structure, could be developed that would enable the initial prevention and/or recurrence of these diseases.

Use of monoclonal antibodies against the region in provasopressin bridging vasopressin and neurophysin moieties (referred to here as "MAP"s), and modified forms of these MAPS, or monoclonal antibodies against vasopressin (referred to here as "MAV"s) and modified forms of these MAVs, or monoclonal antibodies against vasopressin-associated glycopeptide (referred to here as "MAG"s) and modified forms of MAGs, or monoclonal antibodies against tumor-specific regions of GRSA proteins (referred to here as "MAT"s) and modified forms of these MATS, for: a) screening fresh and fixed biopsied material for the presence of breast cancer; b) non-invasive diagnostic imaging of breast cancer in patients and; c) targeting therapy of breast cancer in patients.

MAPS are generated against an undecapeptide, PRG-GKRAMSDL (SEQ ID NO: 1) antigen but primarily recognize the tripeptide bridge structure GKR, and the amino acid residues that skirt this structure. MAGs are generated against an 18-residue polypeptide representing the C-terminal half of the vasopressin-associated glycopeptide (hereinafter "VAG"). MAVs, MAPS, MAGs, and MATS, are designed to recognize what we propose to be the universal provasopressin-related cell-surface antigen(s) on breast cancer called GRSA.

In accordance with the present invention, monoclonal antibodies against the region of provasopressin bridging vasopressin and neurophysin moieties (MAPS), and modified forms of these MAPS, or monoclonal antibodies against vasopressin (MAVs), and modified forms of these MAVs, or monoclonal antibodies against vasopressin-associated glycopeptide (MAGs), and modified forms of these MAGs, or monoclonal antibodies against tumor-specific regions of GRSA proteins (MATS), and modified forms of these MATS, are employed for the screening, in vivo diagnosis, and treatment of breast cancer. From immunohistochemical studies with polyclonal antibodies against vasopressin and polyclonal antibodies against human vasopressin-associated glycopeptide (also called human copeptin), the inventor and, colleagues determined there was a possibility that all breast cancers are reactive with these polyclonal antibodies.

Monoclonal antibodies have been developed not only against vasopressin (MAVs), but also against human VAG, and the bridging structure of human provasopressin. MAGs and MAVs provide positive immunostaining for all breast cancers making them ideal in a single-regimen screening test for breast cancer in fresh and fixed biopsied tissues. Modeling studies show that for GRSA proteins in the plasma membrane of breast cancer cells, not only can the vasopressin moiety be exposed to the outside of the cell but also the glycopeptide region against which MAGs are generated and the provasopressin bridging structure against which MAPS are generated can also be exposed. Thus MAGs, MAPs, MAVs, and MATs also can identify and bind to GRSA proteins on viable cells in culture. They can therefore bind to viable tumor cells in patients, and be used to locate tumors (particularly of the metastatic and/or recurrent disease) in patients and be effectively adapted for targeted immunotherapy. Modification of MAGS, or MAPS or MAVs or MATs, required to make them effective in vivo tools include conversion to Fab and F(ab')$_2$ forms. Diagnostic localization of tumors in patients include (though not exclusively) use of $^{99}$Technetium-, $^{131}$Iodine-, $^{111}$Indium-, and/or ferric-containing-labeled forms of MAGs, MAPs, MAVs, or MATs.

The invention provides a much needed rapid, inexpensive, sensitive, and specific method for: 1) early detection of breast cancer; and 2) identifying and localizing breast cancer, particularly metastatic and/or recurrent disease, in patients. It also provides valuable tools for developing new immuno-targeted treatments, applicable to all patients with breast cancer, that are effective with both primary disease, and with recurrent drug-resistant disease. In this respect it should be useful to all hospitals and physicians examining and treating patients with breast cancer. Detection kits are simple enough to be set up in any local hospital laboratory, and MAGs, MAVs, MAPs and/or MATs and their modified forms can readily be made available to all hospitals treating patients with breast cancer.

Antibodies against an abnormal form of the vasopressin V2 receptor may be used for (a) distinguishing DCIS from ADH, and for; (b) detection and targeting of breast cancer.

We have discovered that breast cancer cells make a tumor-specific abnormal form of vasopressin V2 receptor and predict antibodies directed against this abnormal protein can be used in the early immunohistochemical detection, not only of breast cancer, but also of DCIS. They are also predicted to be valuable in the diagnosis of breast cancer in patients, particularly for detecting and localizing metastatic disease, and in the targeted treatment of breast cancer.

Two forms of vasopressin V2 receptor mRNAs were found by the inventors in breast cancer cells. One of these has a sequence identical to the receptor of normal human tissues; the other is an enlarged form and found to contain the entire 106 bases of intron 2 in addition to the sequence for V2 receptor mRNA. Breast cancer cells produce both these forms of vasopressin V2 receptors. Inclusion of intron 2 introduces a stop colon into the reading frame and therefore the abnormal vasopressin V2 receptor mRNA gives rise to a C-terminally truncated protein lacking the seventh transmembrane segment and carboxyl tail of the normal receptor. We have demonstrated this, and the other vasopressin receptor mRNAs are translated into proteins by the cancer cells through Western analysis using specific antibodies. The antibodies to the abnormal protein are directed against its unique carboxyl terminal region.

The same abnormal receptor was found in SCLC using cell lines NCI-H82, NCI-H146, NCI-H345, and DMS-57 North et al. (1998) *Cancer Research* 58: 1866-1871 and North et al. Vasopressin and Oxytocin. (eds) Zingg et al. Plenum Press, pp. 335-338, 1998). Structures were determined by RT-PCR, cloning, and sequencing. Protein products were verified by Western analysis with specific antibodies.

Breast cancer expresses the vasopressin gene and suspected vasopressin receptor expression always accompanies the vasopressin gene cancer cells. The vasopressin gene is expressed by DCIS but not by various fibrocystic breast conditions, including ADH. Since we expect the abnormal vasopressin V2 receptor will, like breast cancer, be expressed by DCIS, we predict antibodies against this abnormal receptor can be used in methods such as immunohistochemistry to successfully evaluate biopsies and distinguish DCIS and breast cancer from ADH.

Since metastatic as well as localized breast cancer seems to express the heretofore unknown abnormal vasopressin V2 receptor, suitably labeled or modified forms of monoclonal or polyclonal antibodies against this receptor, through injection and different means of detection, are useful in providing a needed very sensitive and specific means of detecting and localizing metastatic and/or early recurrent disease in patients. These antibodies, and their modified form, it is here claimed, are important new tools for effectively targeting different treatments to tumors in patients. This is potentially especially valuable in treating recurrent and generally estrogen-resistant forms of breast cancer.

The disclosed invention can be used for:

1) providing a much needed rapid, inexpensive, sensitive, and specific method for distinguishing DCIS and breast cancer from hyperplastic conditions such as ADH. In this respect it should be useful to all hospitals and physicians examining patients for breast cancer, and of benefit to all women undergoing such diagnosis;

2) providing a much needed sensitive and specific method for non-invasively detecting and localizing recurrent disease and metastatic disease in all breast cancer patients. With refinements, this method will be particularly useful in performing regular screening of all patients who have recovered from breast cancer to detect for any return of the cancer; and 3) providing an effective means for targeting new and effective treatments for all breast cancers including those that are estrogen-sensitive. Modified antibodies can be used either as an additive to treatments with anti-estrogens and chemotherapeutics, or as an effective alternative. Modified forms of the antibodies such as forms carrying a destructive radiochemical or chemical poison, or complexing this immune cells, should be potentially effective in treating all tumors.

Also encompassed by the present invention are methods for distinguishing DCIS from ADH using antibodies against VP or against VP-associated glycopeptide (VAG) or Copeptin; and by performing RT-PCR for VP mRNA on RNA from biopsied material and fixed material from stored tissue blocks.

It is highly likely that all breast cancers express the VP gene. Even though the vasopressin gene is expressed by all examined DCIS, it is generally regarded to be a pre-cursor of invasive breast cancer. The gene is not expressed by various fibrocystic breast conditions, including ADH. The expression of the VP gene is believed by the inventor to be part of the process of oncogenic transformation of cells in the breasts. Vasopressin gene expression produces vasopressin and vasopressin gene-related proteins of approximately 20,000 and 40,000 daltons. Antibodies against VP and VP-associated glycopeptide react with these vasopressin gene products in methods such as immunohistochemistry, and this positive reaction (staining) can be used in a new method to successfully and automatically evaluate biopsies and distinguish DCIS and breast cancer from the benign ADH. Monoclonal antibodies to vasopressin (MAVs) and to vasopressin-related glycopeptide (MAGs) have been developed for this purpose. Alternatively, a method of RT-PCR for VP mRNA, representing the expressed gene, can be utilized, with both fresh and fixed tissue, to identify DCIS.

The vasopressin gene is largely expressed in hypothalamic neurons, where the resultant provasopressin protein is enzymatically cleaved into its peptide hormone components, which include the neuropeptide vasopressin (VP), vasopressin-associated neurophysin (VP-NP), and vasopressin-associated glycopeptide (VAG). Small cell lung cancer (SCLC) tumors also express the vasopressin gene, but the tumor provasopressin protein can remain intact and localize to the cell surface membrane.

The present invention discloses a monoclonal antibody (mAb), designated MAG-1, was raised using a synthetic peptide representing the C-terminal sequence of the VAG domain of human provasopressin. The MAG-1 mAb recognizes NRSA in SCLC cell and tissue lysates by Western analysis, while immunofluorescent cytometric and microscopic analyses indicate that MAG-1 reacts specifically with NRSA on the surface of viable SCLC cells of both the classical and the variant subtype. Immunohistochemical analysis was performed to demonstrate that MAG-1 reacts with human SCLC tumor, but not with normal lung tissue. Additionally, a MAG-1 Fab fragment was generated which was also able to recognize NRSA. This is the disclosure demonstrating that a monoclonal antibody directed to the VAG region of the provasopressin protein has the potential for development into an in vivo diagnostic and therapeutic tool that targets plasma membrane-incorporated NRSA.

A further discovery of the present invention is the ability to distinguish between fibrocystic lesions and cancerous lesions. We have found that if a test samples is positive for provasopressin and negative for the angiotensin II type-2 receptor, a patient is susceptible to invasive breast cancer. If the test sample is positive for both provasopressin and the angiotensin II type-2 receptor, a patient is susceptible to ductal carcinoma in situ. If a test sample is negative for provasopressin and the angiotensin II type-2 receptor, the patient likely has a fibrocystic lesion, such as hyperplastic tissue. Thus, we have discovered a powerful tool whereby health care providers can conclusively distinguish non-invasive fibrocystic tissue from cancerous lesions in test samples from patients suspected of having cancer.

An additional discover of the present invention is that cocktails of chemotherapeutic agents can be administered to a patient in need thereof in combination therapy with pharmaceutical compositions of an antibody, antigen binding fragment, or peptide immunoreactive with provasopressin, whereby the combination therapy is effective at inhibiting proliferation of tumor cells.

II. Definitions

As used herein the term "species" or "animal" refers to mammals, preferably mammals such as humans. Likewise, a "patient" or "subject" to be treated by the method of the invention can mean either a human or non-human animal.

As used herein, "immunoreactive" refers to binding agents, antibodies or fragments thereof that are specific to a tumor target cell antigen, yet if are cross-reactive to other proteins, are not toxic at the levels at which they are formulated for administration to human use. "Specifically binds" means that the binding agent binds to the antigen on the target cell with greater affinity than it binds unrelated antigens. Preferably such affinity is at least 10-fold greater, more preferably at least 100-fold greater, and most preferably at least 1000-fold greater than the affinity of the binding agent for unrelated antigens. The terms "immunoreactive" and "specifically binds" are used interchangeably herein.

The terms "protein", "polypeptide" and "peptide" are used interchangeably herein when referring to a gene product, e.g., as may be encoded by a coding sequence. Peptides of the present invention broadly to refer to portions of the provasopressin amino acid sequence. Preferably, the peptides are portions of the VAG domain of provasopressin. More preferably, the peptides are between 5-50 amino acid residues in length, 5-30 amino acid residues in length, 5-20 amino acid residues in length, or 10-15 amino acid residues in length. The peptides of the present invention are immunoreactive with provasopressin, or portions thereof.

The term "antibody" as used herein, unless indicated otherwise, is used broadly to refer to both antibody molecules and a variety of antibody-derived molecules. Such antibody derived molecules comprise at least one variable region (either a heavy chain of or a light chain variable region), as well as individual antibody light chains, individual antibody heavy chains, chimeric fusions between antibody chains and other molecules, and the like. Functional immunoglobulin fragments according to the present invention may be Fv, scFv, disulfide-linked Fv, Fab, and F(ab')2. Antibodies, or fragments thereof, of the present invention, can be used to image target cells when labeled with a detectable label.

Also encompassed by the term "antibody" are polyclonal antibodies ("pAb"), monoclonal antibodies ("MAb" or "mAb"), preferably IgG$_1$ antibodies; chimeric monoclonal antibodies ("C-MAb"); humanized antibodies; genetically engineered monoclonal antibodies ("G-MAb").

Preferably, the antibody is the monoclonal antibody, MAG-1, which recognizes the 18 C-terminal amino acid residues of the VAG domain of provasopressin. Humanizing antibodies is a technique well-known in the art wherein portions of the framework regions are modified such that they do not cause adverse reactions when administered to a human patient. One of ordinary skill in the art would readily recognize portions of MAG-1 to be mutated such that the antibody was humanized.

The antibodies and peptides of the present invention may be labeled. As used herein, "label" is used to mean a detectable label which is used to visualize the binding of an antibody to its target protein or receptor. Alternatively, antibodies and peptides of the present invention may be labeled with a radiolabel, an iron-related compound, or a toxin which would kill the cell to which it binds. Radiolabels and toxins are well known in the art and include, for example, $^{32}$P, $^{33}$P, $^{43}$K, $^{47}$Sc, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81M}$Kr, $^{87M}$Sr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi and $^{213}$Bi, ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. Iron-related compounds include, for example, $Fe_2O_3$ and $Fe_3O_4$.

"Tumor cell specific antibody" and "tumor cell specific peptide" are defined herein as the ability of an antibody or peptide to specifically bind to the target cell antigen. As used herein, the specificity of the antibody or peptide for a tumor cell antigen can be measured wherein the affinity of the antibody/peptide to the tumor cell antigen is greater then to other cells not associated with the tumor. Antigen binding fragments and peptidomimetics having the same function of specifically binding to a target cell antigen are also contemplated by the present invention.

"Immunoassay" of the present invention include any assay that can be used to determine the presence of a target cell antigen. Non-limiting examples of immunoassays known to one of ordinary skill in the art include immunohistochemistry, ELISAs, MRI and Western Blots.

"Test samples" of the present invention can obtained from patients in an invasive or non-invasive way. Non-invasive test samples include, for example, urine. Invasive test samples include, for example, blood or blood products, lymph tissue or fluid, breast fluid or tissue. Wherein one term is used in the present invention, the other terms are meant to be interchangeable.

"Administering" is defined herein as a means providing the composition to the patient in a manner that results in the composition being inside the patient's body. Such an administration can be by any route including, without limitation, subcutaneous, intradermal, intravenous, intra-arterial, intraperitoneal, and intramuscular.

A physician or veterinarian having ordinary skill in the art can readily determine and prescribe the "effective amount" ($ED_{50}$) of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Each of the embodiments of the present invention can be used as a composition when combined with a pharmaceutically acceptable carrier or excipient. "Carrier" and "excipient" are used interchangeably herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable carrier" is defined herein as a carrier that is physiologically acceptable to the administered patient and that retains the therapeutic properties of the antibodies. Pharmaceutically-acceptable carriers and their formulations are well-known and generally described in, for example, *Remington's pharmaceutical Sciences* (18$^{th}$ Edition, ed. A. Gennaro, Mack Publishing Co., Easton, Pa., 1990). On exemplary pharmaceutically acceptable carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antibodies from the administration site of one organ, or portion of the body, to another organ, or portion of the body. Each carrier must be "acceptable" in the sense of being compatible with the other ingredients of the formulation and not injurious to the patient. Nor should a pharmaceutically acceptable carrier alter the specific activity of the antibodies. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "cancer" is used to mean a condition in which a cell in a patient's body undergoes abnormal, uncontrolled proliferation. Non-limiting examples of cancers include breast cancer, small cell lung cancer, and ductal carcinoma in situ.

As used herein, the term "fibrocystic" is used to mean tissue that is non-cancerous, such as atypical ductal hyperplasia.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. For purposes of this invention, the terms "transformed phenotype of malignant mammalian cells" and "transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

By "treating" a patient suffering from cancer it is meant that the patient's symptoms are partially or totally alleviated, or remain static following treatment according to the invention. A patient that has been treated can exhibit a partial or total alleviation of symptoms and/or tumor load. The term "treatment" is intended to encompass prophylaxis, therapy and cure.

A "therapeutically effective amount" is defined herein an effective amount of composition for producing some desired therapeutic effect by inducing tumor-specific killing of tumor cells in a patient and thereby blocking the biological consequences of that pathway in the treated cells eliminating the tumor cell or preventing it from proliferating, at a reasonable benefit/risk ratio applicable to any medical treatment.

The term "sample" is defined herein as blood, blood product, biopsy tissue, serum, and any other type of fluid or tissue that can be extracted from a patient.

The terms "apoptosis" or "programmed cell death," refers to the physiological process by which unwanted or useless cells are eliminated during development and other normal biological processes. Apoptosis, is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies), which contain ribosomes, morphologically intact mitochondria and nuclear material. In vivo, these apoptotic bodies are rapidly recognized and phagocytized by either macrophages, dendritic cells or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis." Apoptosis can be measured by methods known to those skilled in the art like DNA fragmentation, exposure of Annexin V, activation of caspases, release of cytochrome c, etc. A tumor cell that has been induced to die is termed herein as an "apoptotic tumor cell".

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides.

Operably linked is intended to mean that the nucleotide sequence is linked to a regulatory sequence in a manner which allows expression of the nucleotide sequence. Regulatory sequences are art-recognized and are selected to direct expression of the subject peptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990).

The term "gene construct" refers to a vector, plasmid, viral genome or the like which includes a coding sequence, can transfect cells, preferably mammalian cells, and can cause expression of the antibody, antigen binding fragment, peptide or peptidomimetic of the cells transfected with the construct.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

As used herein, "proliferating" and "proliferation" refer to cells undergoing mitosis.

The term "amino acid residue" is known in the art. In general the abbreviations used herein for designating the amino acids and the protective groups are based on recommendations of the IUPAC-IUB Commission on Biochemical Nomenclature (see Biochemistry (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers. D- and L-α-Amino acids are represented by the following Fischer projections and wedge-and-dash drawings. In the majority of cases, D- and L-amino acids have R- and S-absolute configurations, respectively.

Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into non-peptide compounds with the activity of the parent peptides.

Moreover, as is apparent from the present disclosure, mimetopes of the subject antibodies, antigen binding fragments, peptides, and peptidomimetics can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modifed (Roark et al. in *Peptides: Chemistry and Biology*, G. R. Marshall ed., ESCOM Publisher: Leiden, Netherlands, 1988, p 134). Also, see generally, Session III: Analytic and synthetic methods, in *Peptides: Chemistry and Biology*, G. R. Marshall ed., ESCOM Publisher: Leiden, Netherlands, 1988)

III. Exemplary Embodiments

A. Compounds and Compositions

1. Antibodies and Antigen Binding Fragments Immunoreactive with Provasopressin

Antibodies are immunoreactive with different regions of human provasopressin (e.g., vasopressin (VP), neurophysin (NP) and vasopressin-associated glycopeptide (VAG)), in the cell or as it presents itself as Neurophysin-Related/Glycopeptide-Related Surface Antigen (NRSA/GRSA).

Antibodies of the present invention are immunoreactive with provasopressin. In a preferred embodiment, the antibodies are immunoreactive with the C-terminal portion of VAG domain of human provasopressin. In a preferred embodiment, the antibodies are immunoreactive with the C-terminal 18 amino acid portion of the VAG domain of human provasopressin, characterized by SEQ ID NO: 44. In a preferred embodiment, the antibody is a monoclonal antibody. In a more preferred embodiment, the antibody MAG-1 is produced by a hybridoma having ATCC No. PTA-5322.

Monoclonal antibodies of the present invention include, for example, those immunoreactive with the region of human provasopressin bridging vasopressin and neurophysin moieties (referred to here as "MAP"s), and modified forms of these MAPS, or monoclonal antibodies immunoreactive with vasopressin (referred to here as "MAV"s) and modified forms of these MAVs, or monoclonal antibodies immunoreactive with vasopressin-associated glycopeptide (referred to here as "MAG"s) and modified forms of MAGs, or monoclonal antibodies immunoreactive with tumor-specific regions of GRSA proteins (referred to here as "MAT"s) and modified forms of these MATS.

MAPS are generated against an undecapeptide, PRG-GKRAMSDL (SEQ ID NO: 1) antigen but primarily recognize the tripeptide bridge structure GKR, and the surrounding amino acid residues. MAGs are generated against an 18-residue polypeptide representing the C-terminal half of the human vasopressin-associated glycopeptide (hereinafter "VAG"). MAVs, MAPS, MAGs, and MATS, are designed to recognize the universal provasopressin-related cell-surface antigen(s) on breast cancer, i.e., GRSA, and SCLC, i.e., NRSA.

The present invention discloses a monoclonal antibody (mAb), designated MAG-1, was raised using a synthetic peptide representing the C-terminal sequence of the VAG domain of human provasopressin. The MAG-1 mAb recognizes NRSA in SCLC cell and tissue lysates by Western analysis, while immunofluorescent cytometric and microscopic analyses indicate that MAG-1 reacts specifically with NRSA on the surface of viable SCLC cells of both the classical and the variant subtype. Immunohistochemical analysis was performed to demonstrate that MAG-1 reacts with human SCLC tumor, but not with normal lung tissue. Additionally, a MAG-1 Fab fragment was generated which was also able to recognize NRSA. This is the disclosure demonstrating that a monoclonal antibody directed to the VAG region of the provasopressin protein has the potential for development into an in vivo diagnostic and therapeutic tool that targets plasma membrane-incorporated NRSA.

Antibodies of the present invention also encompass single-chain variable region fragment (scFv), Fab fragments, and F(ab')2 fragments. More preferably, a single-chain variable region fragment (scFv) comprises the amino acid sequence of SEQ ID NO: 2 which is encoded by the nucleic acid sequence of SEQ ID NO: 3.

In a preferred embodiment, the antibody fragment has a variable heavy chain amino acid sequence of SEQ ID NO: 26. In a preferred embodiment, the antibody fragment has a variable light chain amino acid sequence of SEQ ID NO: 27.

A hybridoma cell line which produces the monoclonal antibody MAG-1 was deposited on Jul. 15, 2003, at the American Tissue Culture Collection, 10801 University Blvd., Manassas, Va. 20110-2209, and was given the ATCC accession number PTA-5322. MAG-1 will be maintained under the conditions of the Budapest Treaty. All restrictions upon public access to the deposited material will be irrevocably removed upon the grant of a patent of this application.

Antibodies of the present invention can be made recombinantly. Linkers may be added to the nucleic acid sequences of the heavy and light chains to increase flexibility of the antibody. In the case of a scFv, the linkers are added to connect the Vh and Vl chains and the varying composition can effect solubility, proteolytic stability, flexibility, and folding. In a preferred embodiment, a linker of the present invention has the amino sequence GSTSG (SEQ ID NO: 22). In a preferred embodiment, a linker of the present invention has the amino sequence GGSSRSS (SEQ ID NO: 28). Linkers are well-known in the art and can comprise varied amino acid residues depending on the flexibility needed in the resulting recombinant protein to allow for biological activity.

2. Antibodies Immunoreactive with Angiotensin II Type-2 Receptor

Antibodies of the present invention are immunoreactive with the angiotensin II type-2 receptor. Polyclonal antibodies against the angiotensin II type-2 receptors are commercially available from Santa Cruz Biotechnology (Polyclonal $AT_2$, Santa Cruz, Calif.). Monoclonal antibodies, humanized antibodies, and antigen binding fragments immunoreactive with the angiotensin II type-2 receptor are also contemplated by the present invention.

3. Peptides and Peptidomimetics

One embodiment of the present inventions are peptides, and compositions thereof, which may be used in a screening assay to identify tumor cells expressing neurophysin, VP, pro-VP, or VAG. Peptides of the present invention can comprise 5-50 amino acid residues. More preferably, peptides of the present invention comprise 5-30 amino acid residues. More preferably, peptides of the present invention comprise 5-20 amino acid residues. More preferably, peptides of the present invention comprise 10-15 amino acid residues.

Preferably, the peptide has the sequence TSLSMQYGPLDS (SEQ ID NO: 4); FPFPVRPSPLAM (SEQ ID NO: 5); ILPNTRPSNYLM (SEQ ID NO: 6); HHHRPTPLLQVT (SEQ ID NO: 7); KLKLHDGTPYNL (SEQ ID NO: 8); WQQKGHTPTPMP (SEQ ID NO: 9); QGWPQSSKLGLT (SEQ ID NO: 10); NNQSPHLRPTGS (SEQ ID NO: 11); TTTDMSPHWGLR (SEQ ID NO: 12); TYQSNLGLSSPR (SEQ ID NO: 13); YPYWSNAMSMAS (SEQ ID NO: 14); FPNHALSKRWGI (SEQ ID NO: 15); HQNHLHVPVSWS (SEQ ID NO: 16); TMDPFRSVWPRL (SEQ ID NO: 17); MNYTSTPGPRSW (SEQ ID NO: 18); LLDPYHPRKLSR (SEQ ID NO: 19); IIRGAQVDHSTW (SEQ ID NO: 20); and LWAHSYNFRLLS (SEQ ID NO: 21).

Another aspect of the invention provides a peptide or peptidomimetic, e.g., wherein one or more backbone bonds is replaced or one or more side chains of a naturally occurring amino acid are replaced with sterically and/or electronically similar functional groups.

In certain embodiments, the peptide or peptidomimetic is formulated in a pharmaceutically acceptable excipient.

4. Compositions

Each of the embodiments of the present invention can be used as a composition when combined with a pharmaceutically acceptable carrier or excipient. Pharmaceutically acceptable carrier are physiologically acceptable to the administered patient and that retains the therapeutic properties of the antibodies or peptides with which it is administered. Pharmaceutically-acceptable carriers and their formulations are well-known and generally described in, for example, *Remington's pharmaceutical Sciences* (18$^{th}$ Edition, ed. A. Gennaro, Mack Publishing Co., Easton, Pa., 1990). On exemplary pharmaceutically acceptable carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antibodies or peptides from the administration site of one organ, or portion of the body, to another organ, or portion of the body. Each carrier must be "acceptable" in the sense of being compatible with the other ingredients of the formulation and not injurious to the patient. Nor should a pharmaceutically acceptable carrier alter the specific activity of the antibodies, antigen binding fragments, or peptides.

B. Labels

The antibodies, antigen binding fragments, and peptides of the present invention may be associated with a toxin, a radionuclide, an iron-related compound, or a chemotherapeutic agent which would be toxic when delivered to a cancer cell.

The antibodies, antigen binding fragments, and peptides of the present invention may be associated with detectable label, such as a radionuclide, iron-related compound, or a fluorescent agent for immunodetection of target antigens.

The antibodies and peptides of the present invention which are immunoreactive with the VAG domain of provasopressin can be labeled with a detectable label, such as a radiolabel, a toxin, or fluorescent label Non-limiting examples of radiolabels include, for example, $^{32}$P, $^{33}$P, $^{43}$K, $^{47}$Sc, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81M}$Kr, $^{87M}$Sr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi and $^{213}$Bi.

Non-limiting examples of toxins include, for example, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

Non-limiting examples of fluorescent labels include, for example, FITC, Texas Red, phycoerythrin (PE), and cytochrome c.

Non-limiting examples of iron-related compounds include, for example, magnetic iron-oxide particles, ferric or ferrous particles, $Fe_2O_3$, and $Fe_3O_4$. Iron-related compounds and methods of labeling antibodies and polypeptides can be found, for example, in U.S. Pat. Nos. 4,101,435 and 4,452, 773, and U.S. published applications 20020064502 and 20020136693, all of which are hereby incorporated by reference in their entirety.

Additionally, other labels, such as biotin followed by streptavidin-alkaline phosphatase (AP), horseradish peroxidase (HRP) are contemplated by the present invention.

Methodology for labeling proteins, such as antibodies, antigen binding fragments, and peptides are well known in the art. When the antibodies, antigen binding fragments, and peptides of the present invention are labeled with a radiolabel or toxin, the antibodies, antigen binding fragments, and peptides can be prepared as pharmaceutical compositions which are useful for therapeutic treatment of patients exhibiting increased levels of provasopressin wherein the pharmaceutical compositions are administered to the patient in an effective amount.

C. Chemotherapeutic Agents

Chemotherapeutic agents contemplated by the present invention include chemotherapeutic drugs that are commercially available.

Merely to illustrate, the chemotherapeutic can be an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and/or a DNA repair inhibitor.

Chemotherapeutic agents may be categorized by their mechanism of action into, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine DTIC); antiproliferative/antimitotic antimetabolites such as folic acid analogs (methotrexate); platinum coordination complexes (cisplatin; carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors), angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors. Preferred dosages of the chemotherapeutic agents are consistent with currently prescribed dosages.

D. Variants/Mutants

One embodiment of the invention describes an isolated polypeptide consisting of MAG-b 1, or an antigen binding fragment thereof, which functions as the binding site when folded in the proper 3-D orientation. One embodiment is an isolated polypeptide consisting of SEQ ID NOS: 2, 26, or 27, or a sequence that is at least 70%, 75%, 80%, 85%, 90%, 95%, 98% or 99% homologous to the amino acid sequence represented by SEQ ID NOS: 2, 26, or 27.

One embodiment of the invention comprises variants of the amino acid sequence of MAG-1. Variants of the present invention may have an amino acid sequence that is different by one or more amino acid substitutions to the amino acid sequence disclosed in SEQ ID NOS: 2, 26, or 27. Embodiments which comprise amino acid deletions and/or additions are also contemplated. The variant may have conservative changes (amino acid similarity), wherein a substituted amino acid has similar structural or chemical properties, for example, the replacement of leucine with isoleucine. Guidance in determining which and how many amino acid residues may be substituted, inserted, or deleted without abolishing biological or proposed pharmacological activity may be reasonably inferred in view of this disclosure and may further be found using computer programs well known in the art, for example, DNAStar® software.

Amino acid substitutions may be made, for instance, on the basis of similarity in polarity, charge, solubility, hydrophobicity, hydrophilicity, and/or the amphipathic nature of the residues as long as a biological and/or pharmacological activity of the native molecule is retained.

Negatively charged amino acids include aspartic acid and glutamic acid; positively charged amino acids include lysine and arginine; amino acids with uncharged polar head groups having similar hydrophilicity values include leucine, isoleucine, and valine; amino acids with aliphatic head groups include glycine, alanine; asparagine, glutamine, serine; and amino acids with aromatic side chains include tryptophan, phenylalanine, and tyrosine.

Example substitutions are set forth in Table 1 as follows:

TABLE 1

| Original Residue | Example conservative substitutions |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

"Homology" is a measure of the identity of nucleotide sequences or amino acid sequences. In order to characterize the homology, subject sequences are aligned so that the highest percentage homology (match) is obtained, after introducing gaps, if necessary, to achieve maximum percent homology. N- or C-terminal extensions shall not be construed as affecting homology. "Identity" per se has an art-recognized meaning and can be calculated using published techniques. Computer program methods to determine identity between two sequences, for example, include DNAStar® software (DNAStar Inc. Madison, Wis.); the GCG® program package (Devereux, J., et al. *Nucleic Acids Research* (1984) 12(1): 387); BLASTP, BLASTN, FASTA (Atschul, S. F. et al., *J. Molec Biol* (1990) 215: 403). Homology (identity) as defined herein is determined conventionally using the well-known computer program, BESTFIT® (Wisconsin Sequence Analysis Package, Version 8 for Unix, Genetics Computer Group, University Research Park, 575 Science Drive, Madison, Wis., 53711). When using BESTFIT® or any other sequence alignment program (such as the Clustal algorithm from MegAlign software (DNAStar®) to determine whether a particular sequence is, for example, about 90% homologous to a reference sequence, according to the present invention, the parameters are set such that the percentage of identity is calculated over the full length of the reference nucleotide sequence or amino acid sequence and that gaps in homology of up to about 90% of the total number of nucleotides in the reference sequence are allowed.

Ninety percent of homology is therefore determined, for example, using the BESTFIT® program with parameters set such that the percentage of identity is calculated over the full length of the reference sequence, e.g., SEQ ID NOS: 2, 26, or 27, and wherein up to 10% of the amino acids in the reference sequence may be substituted with another amino acid. Percent homologies are likewise determined, for example, to identify preferred species, within the scope of the claims appended hereto, which reside within the range of about 70% to 100% homology to SEQ ID NOS: 2, 26, or 27, as well as the binding site thereof. As noted above, N- or C-terminal extensions shall not be construed as affecting homology. Thus, when comparing two sequences, the reference sequence is generally the shorter of the two sequences. This means that, for example, if a sequence of 50 nucleotides in length with precise identity to a 50 nucleotide region within a 100 nucleotide polynucleotide is compared, there is 100% homology as opposed to only 50% homology.

Although the naturally polypeptide of SEQ ID NOS: 2, 26, or 27, and a variant polypeptide may only possess 90% identity, they are actually likely to possess a higher degree of similarity, depending on the number of dissimilar codons that are conservative changes. Conservative amino acid substitutions can frequently be made in a protein without altering either the conformation or function of the protein. Similarity between two sequences includes direct matches as well a conserved amino acid substitutes which possess similar structural or chemical properties, e.g., similar charge as described in Table 1.

Percentage similarity (conservative substitutions) between two polypeptides may also be scored by comparing the amino acid sequences of the two polypeptides by using programs well known in the art, including the BESTFIT program, by employing default settings for determining similarity.

A further embodiment of the invention is a heavy or light chain of MAG-1, wherein the amino acid sequence is represented by SEQ ID NOS: 2, 26, or 27. A further embodiment of the invention is a heavy or light chain of MAG-1, or fragment thereof, wherein the amino acid sequence is at least 75%, 80%, 85%, 90%, 95%, 98% or 99% homologous to the amino acid sequence represented by SEQ ID NOS: 2, 26, or 27.

E. Linkers

It may be necessary in some instances to introduce an unstructured polypeptide linker region between a label of the present invention and portions of the antibodies, antigen binding fragments, peptides, or peptidomimetics. The linker can facilitate enhanced flexibility, and/or reduce steric hindrance between any two fragments. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase a subunit. Other examples of naturally occurring linkers include linkers found in the lcI and LexA proteins.

Within the linker, the amino acid sequence may be varied based on the preferred characteristics of the linker as determined empirically or as revealed by modeling. For instance, in addition to a desired length, modeling studies may show that side groups of certain amino acids may interfere with the biological activity, e.g. DNA binding or transcriptional activation, of the protein. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. For example, a linker may contain an amino acid sequence which can be recognized by a protease so that the activity of the chimeric protein could be regulated by cleavage. In some cases, particularly when it is necessary to span a longer distance between subunits or when the domains must be held in a particular configuration, the linker may optionally contain an additional folded domain.

In some embodiments it is preferable that the design of a linker involve an arrangement of domains which requires the linker to span a relatively short distance, preferably less than about 10 Angstroms (Å). However, in certain embodiments, depending, e.g., upon the selected domains and the configuration, the linker may span a distance of up to about 50 Angstroms.

F. Toxins and Imaging Reagents

In certain embodiments, the subject antibodies, antigen binding fragments, peptides and peptidomimetics can be covalently or non-covalently coupled to a cytotoxin or other cell proliferation inhibiting compound, in order to localize delivery of that agent to a tumor cell. For instance, the agent can be selected from the group consisting of alkylating agents, enzyme inhibitors, proliferation inhibitors, lytic agents, DNA or RNA synthesis inhibitors, membrane permeability modifiers, DNA intercalators, metabolites, dichloroethylsulfide derivatives, protein production inhibitors, ribosome inhibitors, inducers of apoptosis, and neurotoxins.

Chemotherapeutics useful as active moieties which when conjugated to antibodies, antigen binding fragments, peptides and peptidomimetics of the present invention are specifically delivered to tumorigenic cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of known cytotoxic agents useful in the present invention are listed, for example, in Goodman et al., "The Pharmacological Basis of Therapeutics," Sixth Edition, A. G. Gilman et al, eds./Macmillan Publishing Co. New York, 1980. These include taxanes, such as paclitaxel (Taxol®) and docetaxel (Taxotere®); nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used; such drugs are known to those skilled in the art and include puromycin, cycloheximide, and ribonuclease.

Most of the chemotherapeutic agents currently in use in treating cancer possess functional groups that are amenable to chemical cross-linking directly with an amine or carboxyl group of an agent of the present invention. For example, free amino groups are available on methotrexate, doxorubicin, daunorubicin, cytosinarabinoside, bleomycin, gemcitabine, fludarabine, and cladribine while free carboxylic acid groups are available on methotrexate, melphalan, and chlorambucil. These functional groups, that is free amino and carboxylic acids, are targets for a variety of homobifunctional and heterobifunctional chemical cross-linking agents which can crosslink these drugs directly to a free amino group of an antibody, antigen binding fragment, peptide or peptidomimetics.

Peptide and polypeptide toxins are also useful as active moieties, and the present invention specifically contemplates embodiments wherein the antibodies, antigen binding fragments, peptides and peptidomimetics of the present invention are coupled to a toxin. In certain preferred embodiments, the antibodies, antigen binding fragments, peptides and peptidomimetics and toxin are both polypeptides and are provided in the form of a fusion protein. Toxins are generally complex toxic products of various organisms including bacteria, plants, etc. Examples of toxins include but are not limited to: ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

The invention further contemplates embodiments in which the antibodies, antigen binding fragments, peptides and peptidomimetics are coupled to a polymer or a functionalized polymer (e.g., a polymer conjugated to another molecule). Preferred examples include water soluble polymers, such as, polyglutamic acid or polyaspartic acid, conjugated to a drug such as a chemotherapeutic or antiangiogenic agent, including, for example, paclitaxel or docetaxel.

In certain preferred embodiments, particularly where the cytotoxic moiety is chemically cross-linked to the antibody, antigen binding fragment, peptide and peptidomimetic moieties, the linkage is hydrolyzable, e.g., such as may be provided by use of an amide or ester group in the linking moiety.

In certain embodiments, the subject antibodies, antigen binding fragments, peptides and peptidomimetics can be coupled with an agent useful in imaging tumors. Such agents include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many embodiments, such secondary functionality will be relatively large, e.g., at least 25 amu in size, and in many instances can be at least 50, 100 or 250 amu in size.

In certain preferred embodiments, the secondary functionality is a chelate moiety for chelating a metal, e.g., a chelator for a radiometal or paramagnetic ion. In preferred embodiments, it is a chelator for a radionuclide useful for radiotherapy or imaging procedures.

Radionuclides useful within the present invention include gamma-emitters, positron-emitters, Auger electron-emitters, X-ray emitters and fluorescence-emitters, with beta- or alpha-emitters preferred for therapeutic use. Examples of radionuclides useful as toxins in radiation therapy include: $^{32}$P, $^{33}$P, $^{43}$K, $^{47}$Sc, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81M}$Kr, $^{87M}$Sr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi and $^{213}$Bi. Preferred therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au and $^{199}$Ag, $^{166}$Ho or $^{177}$Lu. Conditions under which a chelator will coordinate a metal are described, for example, by Gansow et al., U.S. Pat. Nos. 4,831,175, 4,454,106 and 4,472,509. Within the present invention, "radionuclide" and "radiolabel" are interchangeable.

$^{99m}$Tc is a particularly attractive radioisotope for diagnostic applications, as it is readily available to all nuclear medicine departments, is inexpensive, gives minimal patient radiation doses, and has ideal nuclear imaging properties. It has a half-life of six hours which means that rapid targeting of a technetium-labeled antibody is desirable. Accordingly, in certain preferred embodiments, the modified antibodies, antigen binding fragments, peptides and peptidomimetics include a chelating agent for technium.

In still other embodiments, the secondary functionality can be a radiosensitizing agent, e.g., a moiety that increases the sensitivity of cells to radiation. Examples of radiosensitizing agents include nitroimidazoles, metronidazole and misonidazole (see: DeVita, V. T. Jr. in Harrison's Principles of Internal Medicine, p. 68, McGraw-Hill Book Co., N.Y. 1983, which is incorporated herein by reference). The modified antibodies, antigen binding fragments, peptides and peptidomimetics that comprise a radiosensitizing agent as the active moiety are administered and localize at the target cell. Upon exposure of the individual to radiation, the radiosensitizing agent is "excited" and causes the death of the cell.

There are a wide range of moieties which can serve as chelators and which can be derivatized to the antibodies, antigen binding fragments, peptides and peptidomimetics of the present invention. For instance, the chelator can be a derivative of 1,4,7,10-tetraazacyclododecanetetraacetic acid (DOTA), ethylenediaminetetraacetic acid (EDTA), diethylenetriaminepentaacetic acid (DTPA) and 1-p-Isothiocyanato-benzyl-methyl-diethylenetriaminepentaacetic acid (ITC-MX). These chelators typically have groups on the side chain by which the chelator can be used for attachment to subject antibodies, antigen binding fragments, peptides and peptidomimetics. Such groups include, e.g., benzylisothiocyanate, by which the DOTA, DTPA or EDTA can be coupled to, e.g., an amine group.

In one embodiment, the chelate moiety is an "$N_xS_y$," chelate moiety. As defined herein, the term "$N_xS_y$ chelates" includes bifunctional chelators that are capable of coordinately binding a metal or radiometal and, preferably, have $N_2S_2$ or $N_3S$ cores. Exemplary $N_xS_y$ chelates are described, e.g., in Fritzberg et al. (1988) *PNAS* 85:4024-29; and Weber et al. (1990) *Bioconjugate Chem.* 1:431-37; and in the references cited therein.

The Jacobsen et al. PCT application WO 98/12156 provides methods and compositions, i.e. synthetic libraries of binding moieties, for identifying compounds which bind to a metal atom. The approach described in that publication can be used to identify binding moieties which can subsequently be added to antibodies, antigen binding fragments, peptides and peptidomimetics to derive the modified antibodies, antigen binding fragments, peptides and peptidomimetics of the present invention.

A problem frequently encountered with the use of conjugated proteins in radiotherapeutic and radiodiagnostic applications is a potentially dangerous accumulation of the radiolabeled moiety fragments in the kidney. When the conjugate is formed using a acid- or base-labile linker, cleavage of the radioactive chelate from the protein can advantageously occur. If the chelate is of relatively low molecular weight, as most of the subject modified antibodies, antigen binding fragments, peptides and peptidomimetics are expected to be, it is not retained in the kidney and is excreted in the urine, thereby reducing the exposure of the kidney to radioactivity. However, in certain instances, it may be advantageous to utilize acid- or base-labile linkers in the subject ligands for the same reasons they have been used in labeled proteins.

Accordingly, certain of the subject labeled/modified antibodies, antigen binding fragments, peptides and peptidomimetics can be synthesized, by standard methods known in the art, to provide reactive functional groups which can form acid-labile linkages with, e.g., a carbonyl group of the ligand. Examples of suitable acid-labile linkages include hydrazone and thiosemicarbazone functions. These are formed by reacting the oxidized carbohydrate with chelates bearing hydrazide, thiosemicarbazide, and thiocarbazide functions, respectively.

Alternatively, base-cleavable linkers, which have been used for the enhanced clearance of the radiolabel from the kidneys, can be used. See, for example, Weber et al. 1990 *Bioconjug. Chem.* 1:431. The coupling of a bifunctional chelate to antibodies, antigen binding fragments, peptides and peptidomimetics via a hydrazide linkage can incorporate base-sensitive ester moieties in a linker spacer arm. Such an ester-containing linker unit is exemplified by ethylene glycolbis(succinimidyl succinate), (EGS, available from Pierce Chemical Co., Rockford, Ill.), which has two terminal N-hydroxysuccinimide (NHS) ester derivatives of two 1,4-dibutyric acid units, each of which are linked to a single ethylene glycol moiety by two alkyl esters. One NHS ester may be replaced with a suitable amine-containing BFC (for example 2-aminobenzyl DTPA), while the other NHS ester is reacted with a limiting amount of hydrazine. The resulting hydrazide is used for coupling to the antibodies, antigen binding fragments, peptides and peptidomimetics, forming an ligand-BFC linkage containing two alkyl ester functions. Such a conjugate is stable at physiological pH, but readily cleaved at basic pH.

Antibodies, antigen binding fragments, peptides and peptidomimetics labeled by chelation are subject to radiation-induced scission of the chelator and to loss of radioisotope by dissociation of the coordination complex. In some instances, metal dissociated from the complex can be re-complexed, providing more rapid clearance of non-specifically localized isotope and therefore less toxicity to non-target tissues. For example, chelator compounds such as EDTA or DTPA can be infused into patients to provide a pool of chelator to bind released radiometal and facilitate excretion of free radioisotope in the urine.

In still other embodiments, the antibodies, antigen binding fragments, peptides and peptidomimetics are coupled to a Boron addend, such as a carborane. For example, carboranes can be prepared with carboxyl functions on pendant side chains, as is well known in the art. Attachment of such carboranes to an amine functionality, e.g., as may be provided on the antibodies, antigen binding fragments, peptides and peptidomimetics, can be achieved by activation of the carboxyl groups of the carboranes and condensation with the amine group to produce the conjugate. Such modified antibodies, antigen binding fragments, peptides and peptidomimetics can be used for neutron capture therapy.

The present invention also contemplates the modification of the subject peptides with dyes, for example, useful in photodynamic therapy, and used in conjunction with appropriate non-ionizing radiation. The use of light and porphyrins in methods of the present invention is also contemplated and their use in cancer therapy has been reviewed by van den Bergh, Chemistry in Britain, 22: 430-437 (1986), which is incorporated by reference herein in its entirety.

One embodiment of the present invention includes antibodies, antigen binding fragments thereof, peptides, and peptidomimetics labeled with a fluorescent label. Common fluorescent labels include, for example, FITC, PE, Texas Red, cytochrome c, etc. Techniques for labeling polypeptides and proteins are well-known in the art.

One embodiment of the present invention includes antibodies, antigen binding fragments thereof, peptides, and peptidomimetics labeled with a metal compound, such as iron which can be used in MRI imaging and/or for treatment. Iron-containing compounds include both ferrous and ferric-containing compounds, such as ferric-oxides. Specific examples include $Fe_2O_3$ and $Fe_3O_4$. Iron-containing compounds and methods of making iron-coupled antibodies and fragments thereof are described in U.S. Pat. Nos. 4,101,435 and 4,452,773 and published U.S. patent applications 20020064502 and 20020136693, all of which are hereby incorporated by reference in their entireties.

G. Diagnostic Assays

1. Methods of Phenotyping Breast and Lung Samples.

One embodiment of the present invention comprises a method of phenotyping breast tissue samples from patients suspected of having breast cancer, DCIS, or SCLC comprising the steps of (i) obtaining a test biopsy sample from a patient, (ii) rendering the test biopsy sample amenable to immunoassay, (iii) contacting the rendered sample with an antibody or a peptide that is immunoreactive with provasopressin under conditions that allow for binding to provasopressin, and (iv) determining if the cells of the rendered sample overexpress provasopressin compared to a control tissue.

In one embodiment of the present invention, if provasopressin is overexpressed in the biopsy tissue sample, the patient is likely to have invasive breast cancer, DCIS, or small cell lung cancer.

In a further embodiment, the method can additionally comprise contacting the rendered sample with an antibody immunoreactive with the angiotensin II type-2 receptor.

In the present invention, if the tissue biopsy sample is positive for provasopressin and negative for the angiotensin II type-2 receptor, a patient susceptible to invasive breast cancer has been identified.

In the present invention, if the tissue biopsy sample is positive for provasopressin and the angiotensin II type-2 receptor, a patient susceptible to ductal carcinoma in situ has been identified.

In the present invention, if the tissue biopsy sample is negative provasopressin and positive for angiotensin II type-2 receptor, a patient susceptible to atypical ductal hyperplasia has been identified.

2. Methods of Phenotyping Breast Tissue Samples from Patients to Distinguish Fibrocystic and Cancerous Lesions.

One embodiment of the present invention comprises a diagnostic assay wherein fibrocystic tissue can be distinguished from cancerous lesions in breast biopsy samples. The method comprises the steps of obtaining one or more test biopsy sample(s) from a patient, rendering the test biopsy sample amenable to immunoassay, contacting a rendered sample with an antibody or peptide immunoreactive with provasopressin under conditions that allow for binding to provasopressin, contacting a rendered sample with an antibody immunoreactive with an angiotensin II type-2 receptor, and determining if the cells of the rendered samples express one or both of provasopressin and angiotensin II type-2 receptor.

In one embodiment of the present invention, determining if the cells of the rendered samples express one or both of provasopressin and angiotensin II type-2 receptor is accomplished wherein the antibodies and/or peptide are labeled with a detectable label. If the antibodies of the present invention are unlabeled, a secondary antibody can be added to the rendered samples wherein the secondary antibody is labeled with a detectable label. Visualization of the detectable labels can be accomplished using immunohistochemistry methodology as described in the Examples of the instant specification.

In the present invention, if the tissue biopsy sample is positive for provasopressin and negative for the angiotensin II type-2 receptor, a patient susceptible to cancerous lesions, such as invasive breast cancer or SCLC, has been identified.

In the present invention, if the tissue biopsy sample is positive for provasopressin and the angiotensin II type-2 receptor, a patient susceptible to cancerous lesions, such as ductal carcinoma in situ, has been identified.

In the present invention, if the tissue biopsy sample is negative provasopressin and positive for angiotensin II type-2 receptor, a patient susceptible to fibrocystic, non-invasive atypical ductal hyperplasia has been identified.

Antibodies of the Screening Assays

One embodiment of the methods comprises antibodies or antigen binding fragments immunoreactive with human provasopressin. In a preferred embodiment, the antibody immunoreactive with human provasopressin is a polyclonal antibody, a monoclonal antibody, a humanized antibody, a chimeric antibody, a recombinant antibody, or a fragment thereof. In a more preferred embodiment, the antibody is a monoclonal antibody immunoreactive with the C-terminal 18 amino acid residues of the VAG domain of human provasopressin. In a more preferred embodiment, the monoclonal antibody is MAG-1.

In a preferred embodiment, the antigen binding fragment is a single chain variable fragment (scFv), a Fab fragment, a F(ab')2 fragment, a heavy chain, or a light chain immunoreactive with provasopressin. In a more preferred embodiment, the amino acid sequence of the single chain variable fragment (scFv) is characterized by SEQ ID NO: 2, wherein the fragment is encoded by the nucleic acid sequence of SEQ ID NO: 3. In one embodiment, the antigen binding fragment is a heavy chain having the variable heavy chain amino acid sequence of SEQ ID NO: 26. In a preferred embodiment, the antigen binding fragment is light chain having the variable light chain amino acid sequence of SEQ ID NO: 27.

In one embodiment, the antibody immunoreactive with angiotensin II type-2 receptor is a polyclonal antibody, a monoclonal antibody, a humanized antibody, a chimeric antibody, a recombinant antibody, or a fragment thereof. More preferably, the antibody immunoreactive with angiotensin II type-2 receptor is a polyclonal $AT_2$ antibody (Santa Cruz Biochemicals).

Antibodies of the present invention can be unlabeled or labeled with a detectable label as described above. If the antibody of the present invention is unlabeled, a secondary antibody specific for the antibody can be added to the method, wherein the secondary antibody is labeled with a detectable label.

Peptides of the Phenotyping Assays

One embodiment of the present invention are peptides immunoreactive with human provasopressin. In a preferred embodiment, the peptides immunoreactive with the C-terminal VAG domain of human provasopressin. In a more preferred embodiment, the peptide has one of the following amino acid sequences: TSLSMQYGPLDS (SEQ ID NO: 4); FPFPVRPSPLAM (SEQ ID NO: 5); ILPNTRPSNYLM (SEQ ID NO: 6); HHHRPTPLLQVT (SEQ ID NO: 7); KLKLHDGTPYNL (SEQ ID NO: 8); WQQKGHTPTPMP (SEQ ID NO: 9); QGWPQSSKLGLT (SEQ ID NO: 10); NNQSPHLRPTGS (SEQ ID NO: 11); TTTDMSPHWGLR (SEQ ID NO: 12); TYQSNLGLSSPR (SEQ ID NO: 13); YPYWSNAMSMAS (SEQ ID NO: 14); FPNHALSKRWGI (SEQ ID NO: 15); HQNHLHVPVSWS (SEQ ID NO: 16); TMDPFRSVWPRL (SEQ ID NO: 17); MNYTSTPGPRSW (SEQ ID NO: 18); LLDPYHPRKLSR (SEQ ID NO: 19); IIRGAQVDHSTW (SEQ ID NO: 20); and LWAHSYNFRLLS (SEQ ID NO: 21).

Binding of the peptide to provasopressin can be imaged wherein the peptide has been labeled with a detectable label. Acceptable labels have been previously described and are well-known in the art.

H. Kits for Phenotyping Biopsy Tissue Samples for Breast Cancer, Ductal Carcinoma In Situ, or Atypical Ductal Hyperplasia 1. Breast Cancer/Small Cell Lung Cancer One embodiment of the present invention includes for a kit useful for screening a biopsy tissue sample for invasive breast cancer or small cell lung cancer comprising a preparation of an antibody, antigen binding fragment, peptide, or peptidomimetic immunoreactive with provasopressin, wherein the antibody immunoreactive with provasopressin indicates the presence of carcinogenic, invasive breast cancer or small cell lung cancer tissue. If a biopsy tissue sample is positive for provasopressin, an invasive form of cancer, such as breast cancer or small cell lung cancer, as been identified The kit can further comprise a preparation of an antibody, or an antigen binding fragment thereof, immunoreactive with an angiotensin II type-2 receptor. If the biopsy tissue sample is negative for the angiotensin II type-2 receptor, a sample has been confirmed as invasive breast cancer.

2. Ductal Carcinoma In Situ (DCIS).

One embodiment of the present invention includes for a kit useful for screening a biopsy tissue sample for breast ductal carcinoma in situ comprising a preparation of an antibody, antigen binding fragment, peptide, or peptidomimetic immunoreactive with provasopressin, and a preparation of an antibody immunoreactive with an angiotensin II type-2 receptor.

In the present invention, if the biopsy tissue sample is positive for provasopressin and the angiotensin II type-2 receptor, the biopsy tissue sample contains carcinogenic breast ductal carcinoma in situ cells.

3. Atypical Ductal Hyperplasia (ADH).

One embodiment of the present invention includes for a kit useful for screening a biopsy tissue sample for atypical ductal hyperplasia comprising a preparation of an antibody, antigen binding fragment, peptide, or peptidomimetic immunoreactive with provasopressin, and a preparation of an antibody immunoreactive with an angiotensin II type-2 receptor.

In the present invention, if the biopsy tissue sample is negative for provasopressin and positive for the angiotensin II type-2 receptor, the biopsy tissue sample contains hyperplastic cells.

Antibody Preparations of the Kits

One embodiment of the kits are preparations of antibodies or antigen binding fragments immunoreactive with provasopressin. Antibodies and antigen binding fragments can be lyophilized or in solution. Additionally, the preparations can contain stabilizers to increase the shelf-life of the kits, e.g., bovine serum albumin (BSA). Wherein the antibodies and antigen binding fragments are lyophilized, the kit can contain further preparations of solutions to reconstitute the preparations. Acceptable solutions are well known in the art, e.g., PBS.

In one embodiment, the antibody is a polyclonal antibody, a monoclonal antibody, a humanized antibody, a chimeric antibody, a recombinant antibody, or fragment thereof. In a preferred embodiment, the antibody, or fragment thereof is immunoreactive with the C-terminal 18 amino acid residues of the VAG domain of provasopressin. In a preferred embodiment, the antibody, or fragment thereof is immunoreactive with the angiotensin II type-2 receptor.

In a more preferred embodiment, the antibody is a monoclonal antibody immunoreactive with the C-terminal 18 amino acid residues of the VAG domain of provasopressin. In a more preferred embodiment, the monoclonal antibody is MAG-1. In a preferred embodiment, the antigen binding fragment is a single chain variable fragment (scFv), a Fab fragment, a F(ab')2 fragment, a heavy chain, or a light chain immunoreactive with provasopressin. In a more preferred embodiment, the amino acid sequence of the single chain variable fragment (scFv) is characterized by SEQ ID NO: 2, wherein the fragment is encoded by the nucleic acid sequence of SEQ ID NO: 3. In one embodiment, the antigen binding fragment is a heavy chain having the variable heavy chain amino acid sequence of SEQ ID NO: 26. In a preferred embodiment, the antigen binding fragment is light chain having the variable light chain amino acid sequence of SEQ ID NO: 27.

Peptide Preparations of the Kits

One embodiment of the present invention are peptides immunoreactive with the C-terminal region of the VAG region of provasopressin. In a preferred embodiment, the peptide has one of the following amino acid sequences:

```
TSLSMQYGPLDS;         (SEQ ID NO: 4)

FPFPVRPSPLAM;         (SEQ ID NO: 5)

ILPNTRPSNYLM;         (SEQ ID NO: 6)

HHHRPTPLLQVT;         (SEQ ID NO: 7)

KLKLHDGTPYNL;         (SEQ ID NO: 8)

WQQKGHTPTPMP;         (SEQ ID NO: 9)

QGWPQSSKLGLT;         (SEQ ID NO: 10)

NNQSPHLRPTGS;         (SEQ ID NO: 11)

TITDMSPHWGLR;         (SEQ ID NO: 12)

TYQSNLGLSSPR;         (SEQ ID NO: 13)

YPYWSNAMSMAS;         (SEQ ID NO: 14)

-continued
FPNHALSKRWGI;         (SEQ ID NO: 15)

HQNHLHVPVSWS;         (SEQ ID NO: 16)

TMDPFRSVWPRL;         (SEQ ID NO: 17)

MNYTSTPGPRSW;         (SEQ ID NO: 18)

LLDPYHPRKLSR;         (SEQ ID NO: 19)

IIRGAQVDHSTW;         (SEQ ID NO: 20)
and

LWAHSYNFRLLS.         (SEQ ID NO: 21)
```

Binding of the peptide to provasopressin can be imaged wherein the peptide has been labeled with a detectable label. Acceptable labels have been previously described and are well-known in the art.

Peptide preparations can be lyophilized or in solution. Additionally, the preparations can contain stabilizers to increase the shelf-life of the kits, e.g., bovine serum albumin (BSA). Wherein the peptides are lyophilized, the kit can contain further preparations of solutions to reconstitute the preparations. Acceptable solutions are well known in the art, e.g., PBS.

Packaging

Kits of the present invention can further include the components for an ELISA assay for measuring provasopressin and fragments thereof as tumor markers in body fluids. Samples to be tested in this application include, for example, plasma, urine, lymph, breast ductal secretions and products thereof.

Alternatively, preparations of the kits are used in immunoassays, such as immunohistochemistry to test patient tissue biopsy sections.

Units

The compositions of the kit of the present invention can be formulated in single or multiple units for either a single test or multiple tests.

In preferred embodiments, the preparations of the kit are free of pyrogens.

Instructions

Kits of the present invention can include instructions for the use of the compositions in an immunoassay.

I. Methods of Treatment

In one preferred embodiment, pharmaceutical compositions of the present invention can be administered to a patient by any convenient route, including, for example, subcutaneous, intradermal, intravenous, intra-arterial, intraperitoneal, or intramuscular injection.

A physician or veterinarian having ordinary skill in the art can readily determine and prescribe the effective amount ($ED_{50}$) of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Pharmaceutical compositions of the present invention are administered in a therapeutically effective amount which are effective for producing some desired therapeutic effect by inducing tumor-specific killing of tumor cells in a patient and thereby blocking the biological consequences of that pathway in the treated cells eliminating the tumor cell or preventing it from proliferating, at a reasonable benefit/risk ratio applicable to any medical treatment. For the administration of the present pharmaceutical compositions to human patients, the pharmaceutical compositions of the present invention can be formulated by methodology known by one of ordinary skill in the art to be free of pyrogens.

An effective immune response of the present invention is achieved when the patient experiences partial or total alleviation or reduction of signs or symptoms of illness, and specifically includes, without limitation, prolongation of survival. The patient's symptoms remain static, and the tumor burden does not increase.

1. Antibodies, Antigen Binding Fragments, and Peptides Immunoreactive with Provasopressin.

One embodiment of the present invention are methods of treating patient susceptible to breast cancer and DCIS with pharmaceutical compositions of antibodies, antigen binding fragments, and peptides as described above. In a preferred embodiment, the patient receiving treatment is a human patient. Pharmaceutical compositions of the antibodies, antigen binding fragments, and peptides can be administered to a patient in need there of by injection. In a preferred embodiment, the antibodies, antigen binding fragments, or peptides are labeled with a radiolabel or a toxin that kills the target cell upon binding of the antibodies, antigen binding fragments, or peptides to provasopressin.

In one embodiment of the present methods, the toxin is any one of ricin, ricin A chain (ricin toxin), *Pseudomonas* exotoxin (PE), diphtheria toxin (DT), *Clostridium perfringens* phospholipase C (PLC), bovine pancreatic ribonuclease (PBR), pokeweed antiviral protein (PAP), abrin, abrin A chain (abrin toxin), cobra venum factor (CVF), gelonin (GEL), saporin (SAP) modeccin, viscumin or volkensin.

In one embodiment of the present methods, the radiolabel is any one of the following radionuclides: $^{32}$P, $^{33}$P, $^{43}$K, $^{47}$Sc, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81M}$Kr, $^{87M}$Sr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$CS, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi and $^{213}$Bi. Preferred therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au and $^{199}$Ag, $^{166}$Ho or $^{177}$Lu.

2. Combination Therapy

Subject antibodies, antigen binding fragments, peptides and peptidomimetics of the present invention can be used in combination therapy with chemotherapeutic agents. A novel aspect of the present invention is that the MAG-1 antibody in combination with a cocktail of chemotherapeutic agents is effective at inhibiting proliferation of cancerous cells when administered in an effective amount.

Accordingly, one method of treating a cancer of the subject invention involves administering to a subject in need thereof a pharmaceutical composition comprising an antibody immunoreactive with provasopressin; and a pharmaceutical composition comprising a chemotherapeutic agent and epinephrine. Alternatively, the subject in need thereof could be administered a pharmaceutical composition comprising a peptide immunoreactive with provasopressin; and a pharmaceutical composition comprising a chemotherapeutic agent and epinephrine. The pharmaceutical compositions can be administered separately or concomitantly. In one aspect of the present invention, the pharmaceutical compositions are administered in a single formulation. In one aspect of the present invention, the pharmaceutical compositions are administered as separate formulations.

One embodiment of the present invention includes a method of treating a cancer of the present invention comprising administering to a subject in need thereof a pharmaceutical composition comprising antibody immunoreactive with provasopressin; and a pharmaceutical composition comprising a cocktail of dexamethasone, IBMX, and 8-bromoadenosine 3',5'-cyclic monophosphate (8br-cAMP). Alternatively, the method comprises administering a pharmaceutical composition comprising a peptide immunoreactive with provasopressin; and a pharmaceutical composition comprising a cocktail of dexamethasone, IBMX, and 8-bromoadenosine 3',5'-cyclic monophosphate (8br-cAMP).

One embodiment of the present invention includes a method of treating a cancer of the present invention comprising administering to a subject in need thereof a pharmaceutical composition comprising antibody immunoreactive with provasopressin; and a pharmaceutical composition comprising a cocktail of IBMX and forskolin. Alternatively, the method comprises administering a pharmaceutical composition comprising a peptide immunoreactive with provasopressin; and a pharmaceutical composition comprising a cocktail of IBMX and forskolin.

One of ordinary skill in the art could prepare a formulation of any of the chemotherapeutic agents as described above to be administered with a preparation MAG-1 to treat a cancer of the present invention.

Antibodies, antigen binding fragments, and peptides immunoreactive with provasopressin have been described above.

J. Medicaments

Pharmaceutical compositions contemplated by the present invention have been described above. In one embodiment of the present invention, the pharmaceutical compositions are formulated to be free of pyrogens such that they are acceptable for administration to human patients. Testing pharmaceutical compositions for pyrogens and preparing pharmaceutical compositions free of pyrogens are well understood to one of ordinary skill in the art.

One embodiment of the present invention contemplates the use of any of the pharmaceutical compositions of the present invention to make a medicament for treating a cancer of the present invention. Medicaments can be formulated based on the physical characteristics of the patient/subject needing treatment, and can be formulated in single or multiple formulations based on the stage of the cancerous tissue. Medicaments of the present invention can be packaged in a suitable pharmaceutical package with appropriate labels for the distribution to hospitals and clinics wherein the label is for the indication of treating breast cancer, ductal carcinoma in situ, or small cell lung cancer in a subject Medicaments can be packaged as a single or multiple units. Instructions for the dosage and administration of the pharmaceutical compositions of the present invention can be included with the pharmaceutical packages.

IV. Equivalents

Those skilled in the art will recognize, or be able to ascertain using no more than routine experimentation, many equivalents to the specific embodiments of the invention described herein. Such equivalents are intended to be encompassed by the following claims.

All of the above-cited references and publications are hereby incorporated by reference in their entireties.

V. Examples

The present invention is illustrated by the following examples which should not be construed as limiting in any way. The contents of all cited references (including literature references, issued patents, published patent applications as cited throughout this application) are hereby expressly incorporated by reference.

The practice of the present invention will employ, unless otherwise indicated, conventional techniques of cell biology, cell culture, molecular biology, microbiology, and recombinant DNA, which are within the skill of the art. Such techniques are explained fully in the literature. See, for example, Molecular Cloning: A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. S. Higgins eds. 1984); Transcription And Translation (B. D. Hames & S. J. Higgins eds. 1984); and Current Protocols in Immunology, Molecular Biology, Cell Biology, Human Genetics, Protein Science, and Nucleic Acid Chemistry (John Wiley & Sons, Inc., Edison, N.J.).

Materials and Methods

Cultured Cell Lines and Human Tissues

Cultured cell lines were maintained at 37° C. and 5% $CO_2$. The NCI-H82 variant-type SCLC cell line was obtained from the American Type Culture Collection (ATCC) (Manassas, Va.) and cultured in RPMI 1640 (Mediatech, Herndon, Pa.) with 10% FBS (Hyclone, Logan, Utah). The NCI-H345 classical-type SCLC cell line, a gift from Dr. J-J. Legros (Liege, Belgium), was maintained in RPMI 1640 supplemented with 10% FBS, $10^{-8}$ M β-estradiol, $10^{-8}$ M hydrocortisone, 5 μg/ml insulin, 5 μg/ml transferrin, and 5 ng/ml sodium selenite (ITS, Sigma, St. Louis, Mo.), and 0.01 M HEPES. The Lu-165 classical-type SCLC cell line (Terasaki et al. (1994) *Jpn. J. Cancer Res.* 85: 718-722), a gift from Dr. J. Coulson (Liverpool, UK), was maintained in RPMI 1640 with 10% FBS. The Beas-2B transformed human bronchial epithelial cell line, a gift from I. Pitha-Rowe in the laboratory of Dr. E. Dmitrovsky (Dartmouth Medical School), was maintained in LHC-8 media with epinephrine. The mouse myelomal spleen hybrid cell line Sp2/0-Ag14 was obtained from the ATCC and was maintained in DMEM (Mediatech) with 10% FBS. Human SCLC tumor and non-tumor lung tissue samples were obtained either through the Cooperative Human Tissue Network (University of Alabama, Birmingham), or from the Pathology Department of Dartmouth Medical School. Both the non-tumor and SCLC tumor samples were taken from lung tissue that was removed by lobectomy from patients with emphysema. Human hypothalamus tissue was obtained at autopsy with the assistance of Dr. C. Harker Rhodes (Dartmouth Medical School).

Monoclonal Antibodies and Fab Fragments

All procedures involving animals were conducted with the approval of the American Association for the Accreditation of Laboratory Animal Care (AAALAC) certified Dartmouth College and Dartmouth Hitchcock Medical Center Institutional Animal Care and Use Committee (IACUC). MAG-1 mAb was generated against a synthetic 18-amino acid peptide representing the COOH-terminal VAG region of the pro-VP protein (VAGc18: VQLAGAPEPFEPAQPDAY; SEQ ID NO: 23) coupled to bovine thyroglobulin using glutaraldehyde. This complex was used as a 1 mg/ml solution (peptide equivalent concentration) in 0.05 M sodium phosphate (pH 7.0) that had been sonicated with an equal volume of complete Fruend's adjuvant (CFA) to immunize BALB/c mice. A follow-up immunization was performed 21 days later using an mixture of antigen with incomplete Freund's adjuvant (IFA), and spleen cells were harvested after an additional five days. The spleen cells were hybridized with Sp2/0-Ag14 cells, and viable hybridomas were selected using DMEM containing 10% FBS and supplemented with hypoxanthine-aminopterin-thymidine (HAT) (Sigma). Clones were screened for the production of antibodies using $^{125}$I-VAGc18 peptide by displacement RIA (North et al. (1978) *Endocrinology*, 103: 1976-1984). The MAG-1-producing clone was isolated, used to generate ascites fluid in BALB/c mice, and the mAb was purified by immunoaffinity chromatography using a column comprised of VAGc18 conjugated to cyanogen bromide-activated Sepharose 4B (Sigma). MAG-1 was determined to be of isotype $IgG_1$ using a Clonotyping System kit (Southern Biotechnology Associates, Birmingham, Ala.). Fab fragments of MAG-1 were generated using an ImmunoPure $IgG_1$ Fab and $F(ab)_2$ Preparation Kit (Pierce, Rockford, Ill.) following the manufacturer's instructions, and complete ficin digestion of the IgG molecule was confirmed by Western analysis.

Reverse-Transcriptase Polymerase Chain Reaction (RT-PCR) of the Pro-VP Protein

Total RNA was isolated from cultured cells or human tissues using Trizol (Life Technologies, Inc., Rockville, Md.), and 1 μg was used together with oligo(dT) primers and RNase H⁻ reverse transcriptase (Life Technologies, Inc.) in a standard reverse transcription reaction following the manufacture's instructions. Polymerase chain reaction (PCR) was performed using primers AVPfwd (5'-aggatgcctgacaccat-gctg-3'; SEQ ID NO: 24) and AVPrev (5'-attggcggaggtttat-tgtc-3'; SEQ ID NO: 25) in a reaction employing MasterTaq enzyme, TagMaster PCR Enhancer buffer, and a Mastercycler Gradient thermocycler (Eppendorf, Westbury, N.Y.). These primers were designed to span the 2 introns of the VP gene and amplify the entire coding sequence of the pro-VP protein. Cycle conditions were as follows: 1×(95° C. for 5 min), 4×(95° C. for 1 min, 62° C. for 1 min minus 1° C. per cycle, 72° C. for 1 min), 30×(95° C. for 1 min, 57° C. for 1 min, 72° C. for 1 min) followed by a final extension at 72° C. for 10 min.

Reverse-Transcriptase Polymerase Chain Reaction (RT-PCR) of Antibody Fragments

Total RNA was isolated from cultured cells or human tissues using Trizol (Life Technologies, Inc., Rockville, Md.), and 1 μg was used together with oligo(dT) primers and RNase H⁻ reverse transcriptase (Life Technologies, Inc.) in a standard reverse transcription reaction following the manufacture's instructions.

Polymerase chain reaction (PCR) was performed using primers Vh fwd: (5'-AGGTSMARCTGCAGSAGTCWGG-3'; SEQ ID NO: 37); Vh rev: (5'-CCAGGGGCCAGTG-GATAGACAAGCTTGGGTGTCGTTTT-3'; SEQ ID NO: 38); Vl fwd: (5'-GGTGATATCWTGMTGACCCAAWCTC-CACTCTC-3'; SEQ ID NO: 39); and Vl rev: (5'-GGGAA-GATGGATCCAGTTGGTGCAGCATCAGC-3'; SEQ ID NO: 40); in a reaction employing MasterTaq enzyme, TagMaster PCR Enhancer buffer, and a Mastercycler Gradient thermocycler (Eppendorf, Westbury, N.Y.). These primers were designed to span the IgG antibody Fv-DNA and amplify the entire coding sequence of the IgG antibody Fv-DNA. Cycle conditions were as follows: Initial denaturation of 94° C. for 5 minutes; 35 cycles (1 min at 94° C., 2 min at 52° C., 2 min at 72° C.), followed by a final extension at 72° C. for 10 minutes.

Primers were developed based on the MAG-1 sequence with a Sfi1 restriction site for insertion into the pComb3X vector (The Scripps Research Institute, La Jolla, Calif.). Primers used in the PCR reaction for the Vh-Vl orientation are as follows: Vh-fwd: (5'-GGGCCCAGGCGGCCGAGGT-CAAGCTGCAGGAGTCA-3'; SEQ ID NO: 29); Vl-rev: (5'-CCTGGCCGGCCTGGCCTTTKATTTC-CAGYTTGGTCCC-3'; SEQ ID NO: 30); Vh rev: (5'-ACCGGAAGTAGAGCCGGAGACTGTGAGAGTGGAGC C-3'; SEQ ID NO: 31); and Vl fwd: (5'-GGCTCTACTTCCG-GTGATATCGTTATGACCCCAACT-3'; SEQ ID NO: 32). PCR conditions were as follows: initial denaturation of 94° C. for 5 minutes; 35 cycles (30 sec at 90° C., 30 sec at 52° C., 90 sec at 72° C.); followed by a final extension at 72° C. for 10 minutes.

Primers used in the PCR reaction for the Vl-Vh orientation are as follows: Vl-fwd: (5'-GGGCCCAGGCGGC-CGAGCTCGAYATCCAGCTGACTCAGCC-3'; SEQ ID NO: 33); Vh-rev: (5'-CCTGGCCGGCCTGGCCACTAGT-GACAGATGGGGSTGTYGTTTTGG-3'; SEQ ID NO: 34); Vl-rev: (5'-GGAAGATCTAGAGGAACCACCTTT-KATTTCCAGYTTGGTCCC-3'; SEQ ID NO: 35); and Vh-fwd: (5'-GGTGGTTCCTCTAGATCTTCCCTCGAG-GTRMAGCTTCAGGAGTC-3'; SEQ ID NO: 36). PCR conditions were as follows: initial denaturation of 94° C. for 5 minutes; 35 cycles (30 sec at 90° C., 30 sec at 56° C., 90 sec at 72° C.); followed by a final extension at 72° C. for 10 minutes.

For the above primers, the degenerate primers are as follows: K=G or T; R=A or G; Y=C or T; S=G or C; M=A or C; and W=A or T.

Western Analysis

Total protein lysates were prepared from cell or lung tissue samples by extraction in 0.1 M HCl containing 0.1% Tween 20, and protein concentrations were determined using differential absorbance measurements taken at 215 nm and 225 nm (Waddell, W. J. (1956) *J. Lab. Clin. Med.* 48: 311-314). Lysates (40 µg) were separated on 14% gels by SDS-PAGE using in Tris/glycine/SDS buffer (25 mM Tris, 192 mM Glycine, 0.1% SDS, pH 8.3), and the proteins were transferred onto Immobilon-P polyvinylidene difluoride PVDF) membrane (Millipore, Bedford, Mass.) in Tris/glycine/SDS buffer with 20% methanol added, using the MiniProtean 3 system (BioRad, Hercules, Calif.). To block the membranes, they were dried using a Model 583 Gel Dryer (Life Technologies, Inc.), and NRSA/GRSA was detected by sequential incubation with MAG-1 and horseradish peroxidase (HRP)-conjugated protein L (Pierce). For detection of VP-NP, a rabbit polyclonal antibody produced in this laboratory was utilized (North et al. (1993) *Peptides* 14: 303-307). For detection of VP, VAG, or proVP, both monoclonal and polyclonal antibodies were used. This was followed by an HRP-labeled goat anti-rabbit antibody (Gibco BRL). Signal was generated using Lumi-Light Western blotting substrate (Roche, Indianapolis, Ill.), and the membranes were exposed to autoradiography film.

Immunofluorescent Cytometric and Microscopic Analyses

Approximately $10^6$ cultured SCLC cells were incubated with varying dilutions of MAG-1 mAb or Fab in PBS with 0.1% BSA and 0.01% sodium azide, followed by fluorescent isothiocyanate (FITC)-conjugated Fab-specific goat anti-mouse antibody (Sigma). Each step was performed at 4° C., and the cells were washed in the interim. The cells were then fixed in 1% paraformaldehyde at 4° C., washed, and the fluorescence was measured on a FACStar flow cytometer (Becton Dickinson, Mountain View, Calif.). An aliquot of the cells was removed and resuspended in SlowFade Light (Molecular Probes, Eugene, Oreg.) and mounted for visualization using an Axioskop microscope (Zeiss, Thornwood, N.Y.) with Plan NeoFluar optics connected to a BioRad MRC 1024. An $IgG_1$ isotype control (Hybridoma Library, Dartmouth Medical School) was used to assess non-specific binding.

Immunohistochemistry

Sections of 4-6 µm from each formalin-fixed, or acetone-fixed, paraffin-embedded specimens of human SCLC, normal lung, or hypothalamus tissue were stained for NRSA with MAG-1 mAb. Fixed preparations of breast cancer, DCIS, fibrocystic disease, or normal breast tissue were stained for GRSA with MAG-1. All steps were performed at ambient temperature unless otherwise stated. The sections were de-paraffinized by heat exposure (60° C. for 2 h) followed by xylene washes (2×10 min), and tissues were re-hydrated by washes (10 min) in descending concentrations of ethanol (100%-70%). Endogenous peroxidase activity was blocked by incubation in 0.6% hydrogen peroxidase in methanol for 10 min. After washing with PBS (2×3 min), the tissues were subjected to antigen retrieval by proteolytic digestion with trypsin solution (BioGenex, San Ramon, Calif.) for 10 min at 37° C., washed in 95% ethanol for one minute, and then in PBS for 10 min. Slides were blocked with Power Block Universal Blocking Reagent (BioGenex) for 20 min and incubated with MAG-1 mAb (0.25 µg/ml) in PBS with 0.1% BSA overnight at 4° C. Following washes with PBS (2×3 min), the slides were incubated with MultiLink biotinylated goat anti-immunoglobulins solution (BioGenex) for 20 minutes, washed with PBS (2×3 min), and incubated with Label peroxidase-conjugated streptavidin solution (BioGenex) for 20 min. After washing, staining was achieved using 3,3'-diaminobenzidine (DAB) substrate solution (BioGenex) for 2-5 minutes. Tissues were then counterstained with hematoxylin, dehydrated in ascending concentrations of ethanol, washed in xylene, and cover-slipped using SuperMount mounting medium (BioGenex).

Alternatively, sections of 4-6 µm from each formalin-fixed paraffin-embedded specimens of human SCLC, normal lung, or hypothalamus tissue were stained for NRSA with MAG-1 mAb. All steps were performed at ambient temperature unless otherwise stated. The sections were deparaffinized by heat exposure to (60° C. for 10 min) followed by xylene washes (2×5 min), and tissues were re-hydrated by washes (2×5 min) in descending concentrations of ethanol (100%, 95%, and 70%). After washing with PBS (2×5 min), the tissues were subjected to antigen retrieval by 0.01 M sodium citrate (pH 8.5) for 30 min at 80° C. Slides were washed in PBS (2×5 min) and then incubated in Power Block Universal Blocking Reagent (BioGenex) for 5 min and incubated with MAG-1 mAb (1 µg/ml) in PBS with 0.1% BSA and 0.02% Tween 20 and reacted with the tissue sections for 1 h. After washes with PBS (3×5 min), the slides were incubated with MultiLink biotinylated goat anti-immunoglobulins solution (BioGenex) for 30 minutes, washed with PBS (3×5 min), and incubated with Label peroxidase-conjugated streptavidin solution (Bio-Genex) for 30 min. After washing in PBS (3×5 min), staining was achieved using 3,3'-diaminobenzidine (DAB) substrate solution (BioGenex) for 3 minutes. Tissues were then counterstained with hematoxylin, dehydrated in ascending concentrations of ethanol, washed in xylene, and cover-slipped using SuperMount mounting medium (BioGenex).

Example I

Detection of NRSA in SCLC Tumor Tissue and Cultured Cells

Total RNA was extracted from human lung SCLC tumor and non-tumor tissue samples and analyzed for the presence of the vasopressin message by RT-PCR. The PCR reaction was carried out with sequence-specific primers that spanned the two introns of the vasopressin gene.

Only one product was detected in the reactions using RNA extracted from the SCLC tumor, SCLC cultured cells, and human hypothalamus tissue (FIG. 1). This band corresponds in size to that predicted (570 bp) for the VP message employing these particular amplification primers. There was no VP message detected in total RNA extract from the Beas-2B cells, while there was a faint band at ~570 bp detected in the non-tumor lung tissue extract It is possible that this represents VP expression by small, undetected SCLC tumor cells embedded in the lung tissue sample, or expression by pulmonary neuroendocrine cells (Reynolds (2000) *Am. J. Physiol Lung Cell. Mol. Physiol.* 278: L1256-L1263). However, when SDS-PAGE and Western analysis was performed using the MAG-1 mAb and Fab fragment, NRSA was detected in protein extracts from the cultured SCLC cells and tumor tissue, but not in protein extract from the non-tumor lung tissue (FIG. 2A). When cultured SCLC cell protein extract was examined using a polyclonal antibody raised against VP-NP (North, (1993) *Peptides* 14: 303-307), a banding pattern identical to that produced using the MAG-1 mAb was observed (FIG. 2B). The MAG-1 mAb and Fab, as well as the polyclonal anti-VP-NP antibody recognize proteins with molecular masses of ~20 and ~40 kDa, along with what appear to be degradation products and/or deglycosylated forms of the pro-VP protein. The ~20 kDa protein corresponds to the expected size for the pro-VP protein.

Example II

Detection of NRSA at the Surface of Cultured SCLC Cells

NCI-H82 cells were reacted with MAG-1 mAb or Fab, followed by FITC-labeled goat anti-mouse Fab-specific antibody, and fluorescence was measured on a FACStar apparatus FIG. 3). A similar level of staining was observed using a 1 µg/ml concentration of MAG-1 mAb or Fab, however the mean fluorescence measured was increased only ~2-fold when the concentration of Fab was used at 100 µ/ml, whereas it increased ~10-fold when using the mAb at that concentration. Since reactions were performed at 4° C. in the presence of sodium azide to inhibit internalization of proteins from the plasma membrane, these results indicate that the MAG-1 mAb has a higher binding capacity than MAG-1 Fab for NRSA on the surface of cultured SCLC cells. The mAb was also used to detect NRSA on the surface of Lu-165 and NCI-H345 cultured SCLC cells. The intensity of the fluorescence measured after staining with the isotype control mouse mAb was equivalent to that measured in unstained cells. The binding of the MAG-1 mAb to NRSA on the surface of cultured SCLC cells was also assessed by fluorescent microscopy. In all cases, a non-uniform pattern of staining of the cell surface was observed on SCLC cells while almost no staining was present when the isotype control antibody was used (FIG. 4). Propidium iodide was used to stain the nuclei of the NCI-H82 cells for contrast, after the cells had been incubated with MAG-1, FITC-conjugated anti-mouse antibody, and fixed paraformaldehyde (FIG. 4A). When the NCI-H345 and Lu-165 cells were viewed by confocal microscopy, punctuate plasma membrane staining was observed (FIGS. 4B and 4C). While a quantitative assessment concerning the percentage of cells that were found to be immunoreactive with MAG-1 was not made, it is clear that there was a varied level of labeling of individual cells within the population of each cell type.

Example III

Detection of NRSA on Human SCLC Tissue Sections

Figure 5C:
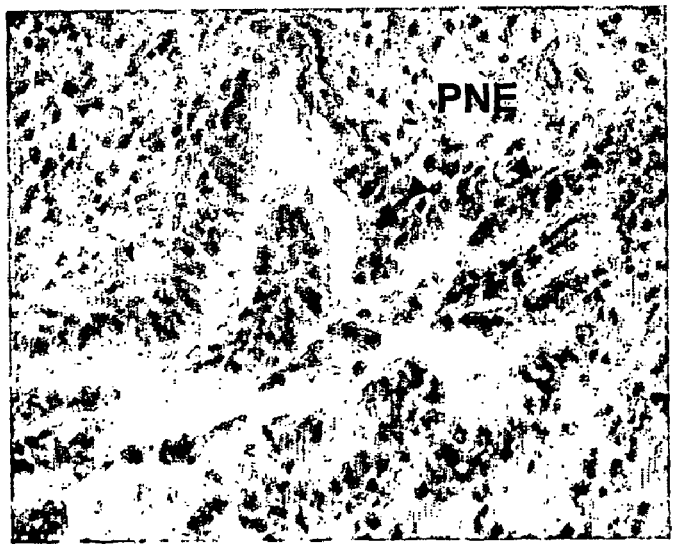
FIG. 5C depicts control normal epithelial cells of the bronchioles of the lung.

Human tissue sections were examined by immunohistochemical analysis using MAG-1, and staining was observed with small cell lung cancer (SCLC) tumor tissue (FIG. 5A), but not with normal lung tissue alveoli (FIG. 5B) or bronchioles FIG. 5C). Both surface and intracellular staining are evident in the SCLC tumor section. Human hypothalamus was used as a positive control, however, only intracellular staining was observed on the hypothalamus tissue section (data not shown).

Example IV

Figure 7:
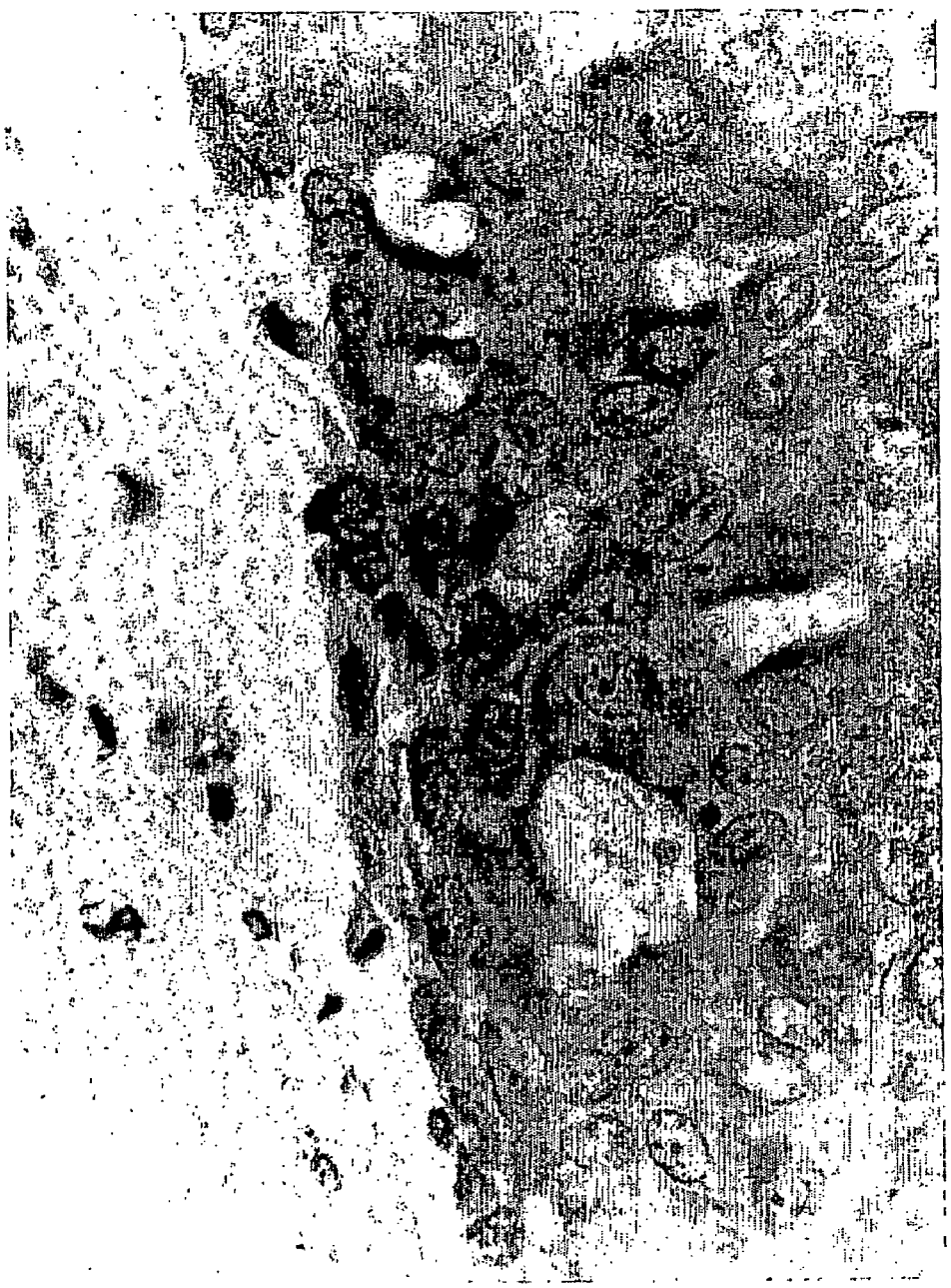
FIG. 7 illustrates staining of human ductal carcinoma in situ (DCIS) tumor tissue sections examined by immunohistochemical analysis using MAG-1.
Figure 8:
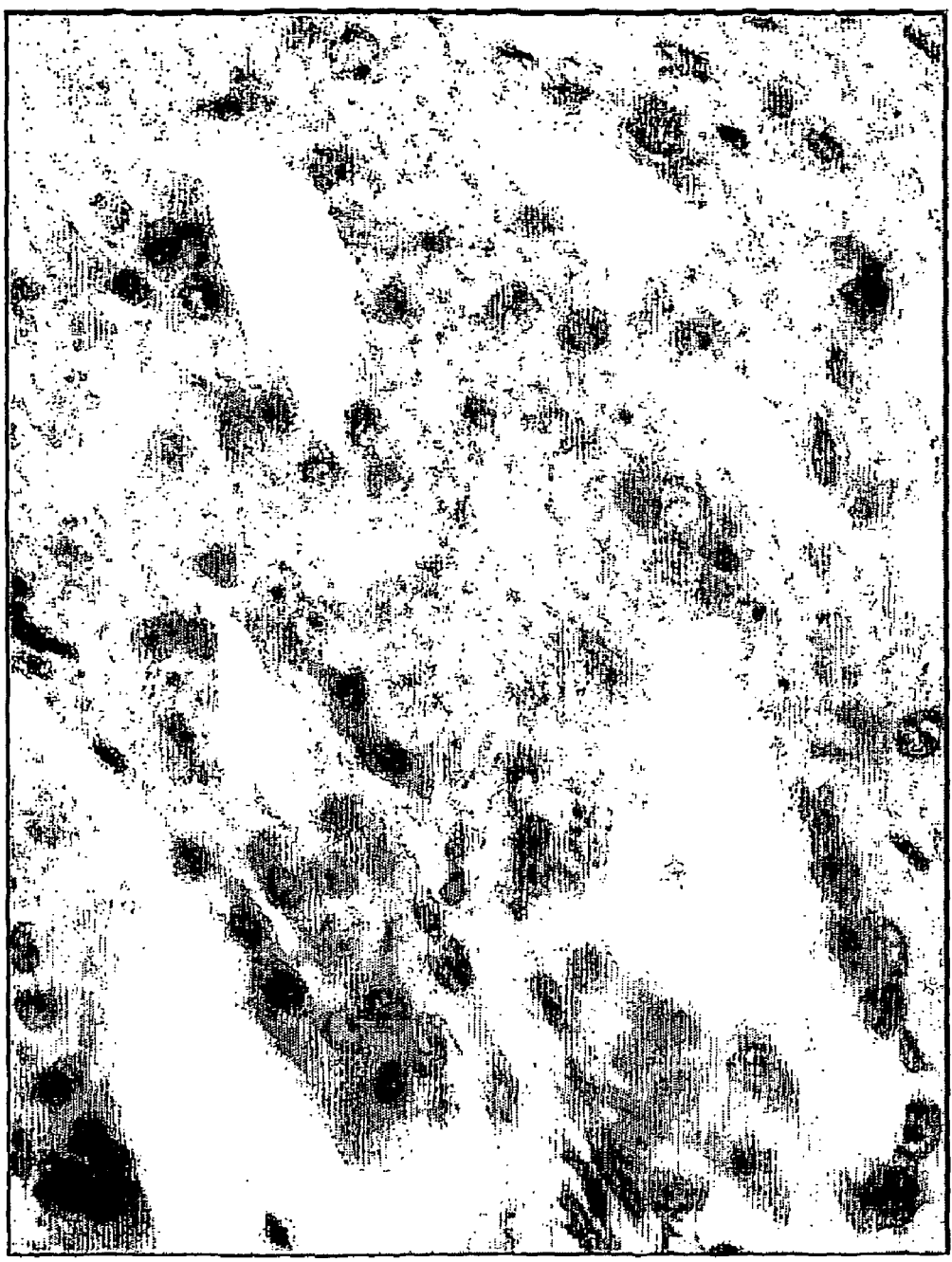
FIG. 8 illustrates lack of staining of human aplastic ductal hyperplasia tumor tissue sections examined by immunohistochemical analysis using MAG-1.

Immunohistochemistry of Ductal Carcinoma In Situ and Aplastic Ductal Hyperplasia Tissue Sections Human tissue sections were examined by immunohistochemical analysis using MAG-1, and staining was observed with ductal carcinoma in situ (DCIS) tumor tissue (FIG. 7), but not with aplastic ductal hyperplasia (FIG. 8).

It will be apparent to those skilled in the art that various modifications and variations can be made in the present invention without departing from the scope or spirit of the invention. Other embodiments of the invention will be apparent to those skilled in the art form consideration of the specification and practice of the invention disclosed herein. It is intended that the specification and examples be considered as exemplary only, with the true scope and spirit of the invention being indicated by the following claims.

REFERENCES

1. Adams et al. (2001) *Cancer Res.* 61: 4750-4755.
2. Birnbaumer, M., et al. (1993) In: P. Gross, D. Richter, G. I. Robertson (eds) *Vasopressin*. John Libbey Eurotext Paris, pp. 19-31.
3. Camier et al. (1979) *FEBS Lett.*, 108: 369-373.
4. Du et al. (2001) *Cancer Letters* 165: 211-218.
5. Drobnik et al. (2000) *J. Physiol. Pharmacol.* 51(3): 521-533.
6. Fay et al. (1994) *Cancer Letters* 82: 167-174.
7. Fay, M. J., et al. (1996) *Peptides* 17:477-481.
8. Friedmann et al. (1993) *Cancer Letters* 75: 79-85.
9. Friedmann et al. (1994) *B. J. Cancer* 69: 260-263.
10. Friedmann et al. (1995) *Neuropeptides* 28: 183-189.
11. Giudice et al. (1979) *J. Biol. Chem.* 254: 11767-11770.
12. Johnson et al. (1998) *J. Natl. Cancer Inst.* (Bethesda) 90: 1335-1345.
13. Junker et al. (2000) *J. Cancer Res. Clin. Oncol.* 126: 361-368.

14. Keegan et al. (November 2002) *Molecular Cancer Therapeutics* 1: 1153-1159.
15. Kortt et al. (2001) *Biomol. Eng.* 18: 95-201.
16. Lauber et al. (1979) *FEBS Lett.*, 97: 343-347.
17. Lauber et al. (1981) *Proc. Natl. Acad. Sci. USA*, 78: 6086-6090.
18. Lin et al. (1979) *Biochem. Biophys. Res. Commun.* 89: 943-950.
19. North et al. (1983) In: F. Greco (ed.), *Biology and Management of Lung Cancer*, pp. 143-169. Boston: Martinus Nijhoff.
20. Moore and Rosenior. (1983) *Prog. Brain Res.*, 60: 253-256.
21. Nicolas et al. (1980) *Proc. Natl. Acad. Sci. USA*, 77: 2587-2591.
22. North et al. (1978) *Endocrinology*, 103: 1976-1984.
23. North et al. (1983) *Prog. Brain Res.* 60: 217-225.
24. North, W. G. In: D. Gash and G. Boer (eds.), *Vasopressin: Principles and Properties*, pp. 175-209. New York: Plenum Press, 1987.
25. North et al. (1989) *Nucl. Med. Commun.* 10: 643-652.
26. William G. North (1991) *J. Clin. Endo. Metab.* 73(6): 1316-1320.
27. North et al. (1993) *Ann. NY Acad. Sci.* 689: 107-121.
28. North et al. (1993) *Peptides* 14: 303-307.
29. North and Yu (1993) *Regulatory Peptides* 45: 209-216.
30. North, W. G., et al. (1995) *Breast cancer Research and Treatment* 34:229-235.
31. North et al. (1997) *Peptides* 18(7): 985-993.
32. North, W. G., et al. (1998) *Cancer Research* 58: 1866-1871.
33. North et al. (1998) *Adv. Exp. Med. Biol.* 449: 335-338.
34. North et al. (1998) *Peptides* 19(10): 1743-1747.
35. North, W. G., et al. (1999) *Peptides* 20:837-842.
36. North, W. G. (2000) *Exp. Physiol.* 85S: 27S-40S.
37. Reynolds et al. (2000) *Am. J. Physiol Lung Cell. Mol. Physiol.* 278: L1256-L1263.
38. Rosenior et al. (1981) *Endocrinology*, 109: 1067-1072.
39. Schmale et al. (1979) *FEBS Lett.* 108: 311-316.
40. Terasaki et al. (1994) *Jpn. J. Cancer Res.* 85: 718-722.
41. Travis et al. (1995) *Cancer* 75: 191-202.
42. Waddell, W. J. (1956) *J. Lab. Clin. Med.* 48: 311-314.
43. Weiner, L. M. (1999) *Semin. Oncol.* 26: 41-50
44. Wistuba et al. (2001) *Semin. Oncol.* 28: 3-13 2001.
45. Todorovska et al. (2001) *J. Immunol. Methods* 248: 47-66.
46. Zangemeister-Wittke and Stahel (1999) *Cell. Mol. Life Sci.* 55: 1585-1598.

We claim:

1. A monoclonal antibody or antigen binding fragment thereof, wherein the antibody is MAG-1 and produced by the hybridoma having ATCC Number PTA-5322.

2. A monoclonal antibody or antigen binding fragment thereof which is immunoreactive with a C-terminal epitope of the VAG domain of provasopressin characterized by SEQ ID NO: 23, wherein the monoclonal antibody is a humanized antibody comprising the complementary determining regions of the MAG-1 antibody of claim 1 and human framework regions.

3. A monoclonal antibody or antigen binding fragment thereof, wherein the antigen binding fragment is a single chain variable fragment, and wherein the single chain variable fragment is characterized by SEQ ID NO: 2.

4. The monoclonal antibody or antigen binding fragment of claim 3, wherein the single chain variable fragment is encoded by the nucleic acid sequence of SEQ ID NO: 3.

5. The monoclonal antibody or antigen binding fragment of claim 1, further comprising a label.

6. The monoclonal antibody or antigen binding fragment of claim 5, wherein the label is selected from the group consisting of a fluorescent label, a radiolabel, a toxin, a metal compound, and biotin.

7. The monoclonal antibody or antigen binding fragment of claim 6, wherein the fluorescent label is selected from the group consisting of Texas Red, phycoerythrin (PE), cytochrome c, and fluorescent isothiocyante (FITC).

8. The monoclonal antibody or antigen binding fragment of claim 6, wherein the radiolabel is selected from the group consisting of $^{32}P$, $^{33}P$, $^{43}K$, $^{47}Sc$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81M}Kr$, $^{87M}Sr$, $^{90}Y$, $^{97}Ru$, $^{99}Tc$, $^{100}Pd$, $^{101}Rh$, $^{103}Pb$, $^{105}Rb$, $^{109}Pd$, $^{111}Ag$, $^{111}In$, $^{113}In$, $^{119}Sb$ $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$.

9. The monoclonal antibody or antigen binding fragment of claim 6, wherein the toxin is selected from the group consisting of ricin, ricin A chain, *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain, cobra venom factor (CVF), gelonin (GEL), saporin (SAP), modeccin, viscumin and volkensin.

10. A pharmaceutical composition comprising the monoclonal antibody or antigen binding fragment of claim 1.

\* \* \* \* \*

```
                         SEQUENCE LISTING

<160> NUMBER OF SEQ ID NOS: 40

<210> SEQ ID NO 1
<211> LENGTH: 11
<212> TYPE: PRT
<213> ORGANISM: Unknown
<220> FEATURE:
<223> OTHER INFORMATION: vasopressin associated glycopeptide

<400> SEQUENCE: 1

Pro Arg Gly Gly Lys Arg Ala Met Ser Asp Leu
1               5                   10

<210> SEQ ID NO 2
<211> LENGTH: 253
<212> TYPE: PRT
<213> ORGANISM: Unknown
<220> FEATURE:
<223> OTHER INFORMATION: vasopressin associated glycopeptide
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
```

<400> SEQUENCE: 2

```
Met Lys Lys Thr Ala Ile Ala Ile Ala Val Ala Leu Ala Gly Phe Ala
1               5                   10                  15

Thr Val Ala Gln Ala Glu Val Lys Leu Xaa Glu Ser Gly Gly Gly Leu
            20                  25                  30

Val His Pro Gly Gly Ser Met Lys Leu Ser Cys Val Ala Ser Gly Phe
        35                  40                  45

Thr Phe Ser Asn Tyr Trp Met Asn Trp Val Arg Gln Ser Pro Glu Lys
    50                  55                  60

Gly Leu Glu Trp Val Ala Glu Ile Arg Leu Lys Ser Asn Asn Tyr Ala
65                  70                  75                  80

Thr His Tyr Ala Glu Ser Val Lys Ala Arg Phe Thr Ile Ser Arg Asp
                85                  90                  95

Asp Ser Lys Ser Thr Val Tyr Leu Gln Met Asn Asn Leu Arg Gly Glu
            100                 105                 110

Asp Thr Gly Ile Tyr Tyr Cys Thr Arg Asp Val Gly Arg Asp Tyr Trp
        115                 120                 125

Gly His Gly Ser Thr Leu Thr Val Ser Gly Ser Thr Ser Gly Asp Ile
    130                 135                 140

Val Met Thr Pro Thr Pro Leu Ser Leu Ser Val Thr Ile Gly Gln Pro
145                 150                 155                 160

Ala Ser Ile Ser Cys Lys Ser Ser Gln Ser Leu Leu Tyr Ser Asn Gly
                165                 170                 175

Lys Thr Tyr Leu Asn Trp Leu Gln Gln Arg Pro Gly Gln Ala Pro Lys
            180                 185                 190

His Leu Met Tyr Gln Val Ser Lys Leu Asp Pro Gly Ile Pro Asp Arg
        195                 200                 205

Phe Ser Gly Ser Gly Ser Lys Thr Asp Phe Thr Leu Xaa Ile Ser Arg
    210                 215                 220

Xaa Glu Ala Glu Asp Trp Xaa Val Tyr Tyr Cys Phe Gln Gly His Ile
225                 230                 235                 240

Ile Arg Thr Arg Thr Gly Xaa Pro Ala Gly Arg Ala Xaa
                245                 250
```

<210> SEQ ID NO 3
<211> LENGTH: 759
<212> TYPE: DNA
<213> ORGANISM: Unknown
<220> FEATURE:
<223> OTHER INFORMATION: vasopressin associated glycopeptide-encoding
      nucleic acid
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t

```
<220> FEATURE:
<221> NAME/KEY: misc_feature
<222> LOCATION: (757)..(758)
<223> OTHER INFORMATION: n is a, c, g, or t

<400> SEQUENCE: 3
atgaaaaaga cagctatcgc gattgcagtg gcactggctg gtttcgctac cgtagcgcag    60
gccgaggtca agctgcntga gtcaggagga ggcttggtgc atcctggagg atccatgaaa   120
ctctcctgtg ttgcctctgg attcactttc agtaactact ggatgaactg ggtccgccag   180
tctccagaga agggggcttga gtgggttgct gaaattagat tgaaatctaa taattatgca   240
acacattatg cggagtctgt gaaagcgagg ttcaccatct caagagatga ttccaaaagt   300
actgtctacc tgcaaatgaa caacttaaga ggtgaagaca ctggcattta ttactgtacc   360
agggacgtgg gacgtgacta ctggggccat ggctccactc tcacagtctc cggctctact   420
tccggtgata tcgttatgac cccaactcca ctctctttgt cggttaccat tggacaacca   480
gcctctatct cttgcaagtc aagtcagagc ctcttatata gtaatggaaa gacatatttg   540
aattggttac aacagaggcc tggccaggct ccaaagcacc taatgtatca ggtgtccaaa   600
ctggaccctg gcatccctga caggttcagt ggcagtggat caaaaacaga ttttacacct   660
naaatcagca gagnggaggc tgaagattgg gnagtttatt actgcttcca gggacatata   720
atccgtactc gtacgggccc nccagctgga agggcannc                          759

<210> SEQ ID NO 4
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 4

Thr Ser Leu Ser Met Gln Tyr Gly Pro Leu Asp Ser
1               5                  10

<210> SEQ ID NO 5
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 5

Phe Pro Phe Pro Val Arg Pro Ser Pro Leu Ala Met
1               5                  10

<210> SEQ ID NO 6
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 6

Ile Leu Pro Asn Thr Arg Pro Ser Asn Tyr Leu Met
1               5                  10

<210> SEQ ID NO 7
<211> LENGTH: 12
<212> TYPE: PRT
<213> ORGANISM: Unknown
<220> FEATURE:
<223> OTHER INFORMATION: vasopressin associated glycopeptide
```

```
<400> SEQUENCE: 7

His His His Arg Pro Thr Pro Leu Leu Gln Val Thr
1               5                   10

<210> SEQ ID NO 8
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 8

Lys Leu Lys Leu His Asp Gly Thr Pro Tyr Asn Leu
1               5                   10

<210> SEQ ID NO 9
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 9

Trp Gln Gln Lys Gly His Thr Pro Thr Pro Met Pro
1               5                   10

<210> SEQ ID NO 10
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 10

Gln Gly Trp Pro Gln Ser Ser Lys Leu Gly Leu Thr
1               5                   10

<210> SEQ ID NO 11
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 11

Asn Asn Gln Ser Pro His Leu Arg Pro Thr Gly Ser
1               5                   10

<210> SEQ ID NO 12
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 12

Thr Ile Thr Asp Met Ser Pro His Gln Gly Leu Arg
1               5                   10

<210> SEQ ID NO 13
<211> LENGTH: 12
<212> TYPE: PRT
<213> ORGANISM: Unknown
<220> FEATURE:
<223> OTHER INFORMATION: vasopressin associated glycopeptide
```

```
<400> SEQUENCE: 13

Thr Tyr Gln Ser Asn Leu Gly Leu Ser Ser Pro Arg
1               5                   10

<210> SEQ ID NO 14
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 14

Tyr Pro Tyr Trp Ser Asn Ala Met Ser Met Ala Ser
1               5                   10

<210> SEQ ID NO 15
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 15

Phe Pro Asn His Ala Leu Ser Lys Arg Trp Gly Ile
1               5                   10

<210> SEQ ID NO 16
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 16

His Gln Asn His Leu His Val Pro Val Ser Trp Ser
1               5                   10

<210> SEQ ID NO 17
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 17

Thr Met Asp Pro Phe Arg Ser Val Trp Pro Arg Leu
1               5                   10

<210> SEQ ID NO 18
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 18

Met Asn Tyr Thr Ser Thr Pro Gly Pro Arg Ser Trp
1               5                   10

<210> SEQ ID NO 19
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 19
```

-continued

```
Leu Leu Asp Pro Tyr His Pro Arg Lys Leu Ser Arg
1               5                   10

<210> SEQ ID NO 20
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 20

Ile Ile Arg Gly Ala Gln Val Asp His Ser Thr Trp
1               5                   10

<210> SEQ ID NO 21
<211> LENGTH: 12
<212> TYPE: PRT
<213> ORGANISM: Unknown
<220> FEATURE:
<223> OTHER INFORMATION: vasopressin associated glycopeptide

<400> SEQUENCE: 21

Leu Trp Ala His Ser Tyr Asn Phe Arg Leu Leu Ser
1               5                   10

<210> SEQ ID NO 22
<211> LENGTH: 5
<212> TYPE: PRT
<213> ORGANISM: Unknown
<220> FEATURE:
<223> OTHER INFORMATION: vasopressin associated glycopeptide

<400> SEQUENCE: 22

Gly Ser Thr Ser Gly
1               5

<210> SEQ ID NO 23
<211> LENGTH: 18
<212> TYPE: PRT
<213> ORGANISM: Unknown
<220> FEATURE:
<223> OTHER INFORMATION: vasopressin associated glycopeptide

<400> SEQUENCE: 23

Val Gln Leu Ala Gly Ala Pro Glu Pro Phe Glu Arg Ala Gln Pro Asp
1               5                   10                  15

Ala Tyr

<210> SEQ ID NO 24
<211> LENGTH: 21
<212> TYPE: DNA
<213> ORGANISM: Unknown
<220> FEATURE:
<223> OTHER INFORMATION: oligonucleotide primer

<400> SEQUENCE: 24
aggatgcctg acaccatgct g                                            21

<210> SEQ ID NO 25
<211> LENGTH: 20
<212> TYPE: DNA
<213> ORGANISM: Unknown
<220> FEATURE:
<223> OTHER INFORMATION: oligonucleotide primer

<400> SEQUENCE: 25
```

```
attggcggag gtttattgtc                                              20
```

<210> SEQ ID NO 26
<211> LENGTH: 137
<212> TYPE: PRT
<213> ORGANISM: Unknown
<220> FEATURE:
<223> OTHER INFORMATION: Variable heavy chain of scFv1
<220> FEATURE:
<221> NAME/KEY: misc_feature
<222> LOCATION: (26)..(26)
<223> OTHER INFORMATION: Xaa can be any naturally occurring amino acid

<400> SEQUENCE: 26

```
Met Lys Lys Thr Ala Ile Ala Ile Ala Val Ala Leu Ala Gly Phe Ala
1               5                   10                  15

Thr Val Ala Gln Ala Glu Val Lys Leu Xaa Glu Ser Gly Gly Gly Leu
            20                  25                  30

Val His Pro Gly Gly Ser Met Lys Leu Ser Cys Val Ala Ser Gly Phe
        35                  40                  45

Thr Phe Ser Asn Tyr Trp Met Asn Trp Val Arg Gln Ser Pro Glu Lys
    50                  55                  60

Gly Leu Glu Trp Val Ala Glu Ile Arg Leu Lys Ser Asn Asn Tyr Ala
65                  70                  75                  80

Thr His Tyr Ala Glu Ser Val Lys Ala Arg Phe Thr Ile Ser Arg Asp
                85                  90                  95

Asp Ser Lys Ser Thr Val Tyr Leu Gln Met Asn Asn Leu Arg Gly Glu
            100                 105                 110

Asp Thr Gly Ile Tyr Tyr Cys Thr Arg Asp Val Gly Arg Asp Tyr Trp
        115                 120                 125

Gly His Gly Ser Thr Leu Thr Val Ser
    130                 135
```

<210> SEQ ID NO 27
<211> LENGTH: 111
<212> TYPE: PRT
<213> ORGANISM: Unknown
<220> FEATURE:
<223> OTHER INFORMATION: Variable heavy chain of scFv1
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid

<400> SEQUENCE: 27

```
Asp Ile Val Met Thr Pro Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30
```

-continued

```
Asn Gly Lys Thr Tyr Leu Asn Trp Leu Gln Gln Arg Pro Gly Gln Ala
            35                  40                  45

Pro Lys His Leu Met Tyr Gln Val Ser Lys Leu Asp Pro Gly Ile Pro
        50                  55                  60

Asp Arg Phe Ser Gly Ser Gly Ser Lys Thr Asp Phe Thr Leu Xaa Ile
65                  70                  75                  80

Ser Arg Xaa Glu Ala Glu Asp Trp Xaa Val Tyr Tyr Cys Phe Gln Gly
                85                  90                  95

His Ile Ile Arg Thr Arg Thr Gly Xaa Pro Ala Gly Arg Ala Xaa
            100                 105                 110
```

<210> SEQ ID NO 28
<211> LENGTH: 7
<212> TYPE: PRT
<213> ORGANISM: Unknown
<220> FEATURE:
<223> OTHER INFORMATION: vasopressin associated glycopeptide

<400> SEQUENCE: 28

Gly Gly Ser Ser Arg Ser Ser
1               5

<210> SEQ ID NO 29
<211> LENGTH: 35
<212> TYPE: DNA
<213> ORGANISM: Unknown
<220> FEATURE:
<223> OTHER INFORMATION: oligonucleotide primer

<400> SEQUENCE: 29
gggcccaggc ggccgaggtc aagctgcagg agtca                           35

<210> SEQ ID NO 30
<211> LENGTH: 37
<212> TYPE: DNA
<213> ORGANISM: Unknown
<220> FEATURE:
<223> OTHER INFORMATION: oligonucleotide primer

<400> SEQUENCE: 30
cctggccggc ctggcctttk atttccagyt tggtccc                         37

<210> SEQ ID NO 31
<211> LENGTH: 36
<212> TYPE: DNA
<213> ORGANISM: Unknown
<220> FEATURE:
<223> OTHER INFORMATION: oligonucleotide primer

<400> SEQUENCE: 31
accggaagta gagccggaga ctgtgagagt ggagcc                          36

<210> SEQ ID NO 32
<211> LENGTH: 36
<212> TYPE: DNA
<213> ORGANISM: Unknown
<220> FEATURE:
<223> OTHER INFORMATION: oligonucleotide primer

<400> SEQUENCE: 32
ggctctactt ccggtgatat cgttatgacc ccaact                          36

<210> SEQ ID NO 33

```
<210> SEQ ID NO 33
<211> LENGTH: 40
<212> TYPE: DNA
<213> ORGANISM: Unknown
<220> FEATURE:
<223> OTHER INFORMATION: oligonucleotide primer

<400> SEQUENCE: 33
gggcccaggc ggccgagctc gayatccagc tgactcagcc                               40

<210> SEQ ID NO 34
<211> LENGTH: 45
<212> TYPE: DNA
<213> ORGANISM: Unknown
<220> FEATURE:
<223> OTHER INFORMATION: oligonucleotide primer

<400> SEQUENCE: 34
cctggccggc ctggccacta gtgacagatg gggstgtygt tttgg                        45

<210> SEQ ID NO 35
<211> LENGTH: 42
<212> TYPE: DNA
<213> ORGANISM: Unknown
<220> FEATURE:
<223> OTHER INFORMATION: oligonucleotide primer

<400> SEQUENCE: 35
ggaagatcta gaggaaccac ctttkatttc cagyttggtc cc                            42

<210> SEQ ID NO 36
<211> LENGTH: 44
<212> TYPE: DNA
<213> ORGANISM: Unknown
<220> FEATURE:
<223> OTHER INFORMATION: oligonucleotide primer

<400> SEQUENCE: 36
ggtggttcct ctagatcttc cctcgaggtr magcttcagg agtc                         44

<210> SEQ ID NO 37
<211> LENGTH: 22
<212> TYPE: DNA
<213> ORGANISM: Unknown
<220> FEATURE:
<223> OTHER INFORMATION: oligonucleotide primer

<400> SEQUENCE: 37
aggtsmarct gcagsagtcw gg                                                  22

<210> SEQ ID NO 38
<211> LENGTH: 38
<212> TYPE: DNA
<213> ORGANISM: Unknown
<220> FEATURE:
<223> OTHER INFORMATION: oligonucleotide primer

<400> SEQUENCE: 38
ccaggggcca gtggatagac aagcttgggt gtcgtttt                                 38

<210> SEQ ID NO 39
<211> LENGTH: 32
<212> TYPE: DNA
<213> ORGANISM: Unknown
<220> FEATURE:
<223> OTHER INFORMATION: oligonucleotide primer

<400> SEQUENCE: 39
```

```
ggtgatatcw tgmtgaccca awctccactc tc                          32

<210> SEQ ID NO 40
<211> LENGTH: 32
<212> TYPE: DNA
<213> ORGANISM: Unknown
<220> FEATURE:
<223> OTHER INFORMATION: oligonucleotide primer

<400> SEQUENCE: 40
gggaagatgg atccagttgg tgcagcatca gc                          32
```